United States Patent
Lopez-Tapia et al.

(10) Patent No.: US 9,624,201 B2
(45) Date of Patent: Apr. 18, 2017

(54) INHIBITORS OF BRUTON'S TYROSINE KINASE

(71) Applicants: Hoffmann-La Roche Inc., Nutley, NJ (US); Chugai Seiyaku Kabushiki Kaisha, Tokyo (JP)

(72) Inventors: Francisco Javier Lopez-Tapia, Honolulu, HI (US); Sung-Sau So, Verona, NJ (US); Qi Qiao, San Diego, CA (US); Romyr Dominique, Ridgewood, NJ (US)

(73) Assignees: HOFFMANN-LA ROCHE INC., Nutley, NJ (US); CHUGAI PHARMACEUTICAL CO., Tokyo (JP)

( * ) Notice: Subject to any disclaimer, the term of this patent is extended or adjusted under 35 U.S.C. 154(b) by 0 days.

(21) Appl. No.: 15/102,315

(22) PCT Filed: Dec. 10, 2014

(86) PCT No.: PCT/EP2014/077113
§ 371 (c)(1),
(2) Date: Jun. 7, 2016

(87) PCT Pub. No.: WO2015/086635
PCT Pub. Date: Jun. 18, 2015

(65) Prior Publication Data
US 2016/0318907 A1  Nov. 3, 2016

Related U.S. Application Data

(60) Provisional application No. 61/915,576, filed on Dec. 13, 2013.

(51) Int. Cl.
C07D 403/06 (2006.01)
C07D 403/14 (2006.01)
C07D 401/14 (2006.01)
C07D 409/14 (2006.01)

(52) U.S. Cl.
CPC ......... *C07D 403/06* (2013.01); *C07D 401/14* (2013.01); *C07D 403/14* (2013.01); *C07D 409/14* (2013.01)

(58) Field of Classification Search
None
See application file for complete search history.

(56) References Cited

U.S. PATENT DOCUMENTS

2012/0208811 A1* 8/2012 Taka .................. A61K 31/4184
514/234.5

OTHER PUBLICATIONS

Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Burger et al., Bruton's Tyrosine Kinase (BTK) Inhibitors in Clinical Trials. Current Hematologic Malignancy Report, 2014, 9, 44-49.*

* cited by examiner

*Primary Examiner* — Matthew Coughlin
*Assistant Examiner* — Po-Chih Chen

(57) ABSTRACT

This application discloses compounds according to generic Formula (I): wherein all variables are defined as described herein, which inhibit Btk. The compounds disclosed herein are useful to modulate the activity of Btk and treat diseases associated with excessive Btk activity. The compounds are useful for the treatment of oncological, auto-immune, and inflammatory diseases caused by aberrant B-cell activation. Also disclosed are compositions containing compounds of Formula (I) and at least one carrier, diluent or excipient.

(I)

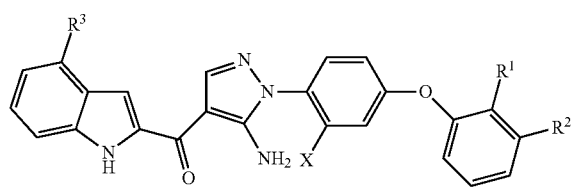

22 Claims, No Drawings

INHIBITORS OF BRUTON'S TYROSINE KINASE

CROSS-REFERENCE TO RELATED APPLICATIONS

This application is a National Stage Application of PCT/EP2014/077113 filed Dec. 10, 2014, which claims priority from U.S. Provisional Patent Application No. 61/915,576, filed on Dec. 13, 2013.

FIELD OF THE INVENTION

The present invention relates to the use of novel compounds which inhibit Btk and are useful for the treatment of oncological, auto-immune, and inflammatory diseases caused by aberrant B-cell activation.

BACKGROUND OF THE INVENTION

Protein kinases constitute one of the largest families of human enzymes and regulate many different signaling processes by adding phosphate groups to proteins (T. Hunter, *Cell* 1987 50:823-829). Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a target to modulate cellular function with small molecular kinase inhibitors and thus make good drug design targets. In addition to treatment of kinase-mediated disease processes, selective and efficacious inhibitors of kinase activity are also useful for investigation of cell signaling processes and identification of other cellular targets of therapeutic interest.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. *Annu Rev Med* 2004 55:477). Therefore inhibitors of the protein kinases that play a role in B-cell activation should be useful therapeutics for B-cell mediated disease pathology such as autoantibody production.

Signaling through the B-cell receptor (BCR) controls a range of B-cell responses including proliferation and differentiation into mature antibody producing cells. The BCR is a key regulatory point for B-cell activity and aberrant signaling can cause deregulated B-cell proliferation and formation of pathogenic autoantibodies that lead to multiple autoimmune and/or inflammatory diseases. Bruton's Tyrosine Kinase (Btk) is a non-BCR associated kinase that is membrane proximal and immediately downstream from BCR. Lack of Btk has been shown to block BCR signaling and therefore inhibition of Btk could be a useful therapeutic approach to block B-cell mediated disease processes.

Btk is a member of the Tec family of tyrosine kinases, and has been shown to be a critical regulator of early B-cell development and mature B-cell activation and survival (Khan et al. *Immunity* 1995 3:283; Ellmeier et al. *J. Exp. Med.* 2000 192:1611). Mutation of Btk in humans leads to the condition X-linked agammaglobulinemia (XLA) (reviewed in Rosen et al. *New Eng. J. Med.* 1995 333:431 and Lindvall et al. *Immunol. Rev.* 2005 203:200). These patients are immunocompromised and show impaired maturation of B-cells, decreased immunoglobulin and peripheral B-cell levels, diminished T-cell independent immune responses as well as attenuated calcium mobilization following BCR stimulation.

Evidence for a role for Btk in autoimmune and inflammatory diseases has also been provided by Btk-deficient mouse models. In preclinical murine models of systemic lupus erythematosus (SLE), Btk-deficient mice show marked amelioration of disease progression. In addition, Btk-deficient mice are resistant to collagen-induced arthritis (Jansson and Holmdahl *Clin. Exp. Immunol.* 1993 94:459). A selective Btk inhibitor has been demonstrated dose-dependent efficacy in a mouse arthritis model (Z. Pan et al., *Chem. Med Chem.* 2007 2:58-61).

Btk is also expressed by cells other than B-cells that may be involved in disease processes. For example, Btk is expressed by mast cells and Btk-deficient bone marrow derived mast cells demonstrate impaired antigen induced degranulation (Iwaki et al. *J. Biol. Chem.* 2005 280:40261). This shows Btk could be useful to treat pathological mast cells responses such as allergy and asthma. Also monocytes from XLA patients, in which Btk activity is absent, show decreased TNF alpha production following stimulation (Horwood et al. *J Exp Med* 197:1603, 2003). Therefore TNF alpha mediated inflammation could be modulated by small molecular Btk inhibitors. Also, Btk has been reported to play a role in apoptosis (Islam and Smith *Immunol. Rev.* 2000 178:49) and thus Btk inhibitors would be useful for the treatment of certain B-cell lymphomas and leukemias (Feldhahn et al. *J. Exp. Med.* 2005 201:1837).

SUMMARY OF THE INVENTION

The present application provides the Btk inhibitor compounds of Formula I, methods of use thereof, as described herein below:

The application provides a compound of Formula I,

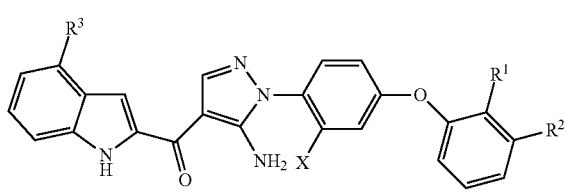

wherein:
R$^1$ is H or halo;
R$^2$ is H, halo, or cyano;
R$^3$ is R$^4$ or R$^5$;
 R$^4$ is halo or cyano;
 R$^5$ is phenyl, heteroaryl, —C(=O)R$^{5'}$, lower alkyl, or benzyl, optionally substituted with one or more R$^{5'}$;
 R$^{5'}$ is lower alkyl, cyano, hydroxyl, heterocycloalkyl, phenyl, amino, alkyl amino, dialkyl amino, or lower alkoxy; and
X is lower alkyl or halo;
or a pharmaceutically acceptable salt thereof.

The application provides a method for treating an inflammatory and/or autoimmune condition comprising administering to a patient in need thereof a therapeutically effective amount of the compound of Formula I.

The application provides a pharmaceutical composition comprising the compound of Formula I, admixed with at least one pharmaceutically acceptable carrier, excipient or diluent.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

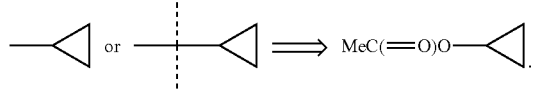

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds of Formulae I may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— $\leftrightarrows$ —C(—OH)=CH—), amide/imidic acid (—C(=O)—NH— $\leftrightarrows$ —C(—OH)=N—) and amidine (—C(=NR)—NH— $\leftrightarrows$ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl", "haloalkylheteroaryl", "arylalkylheterocyclyl", "alkylcarbonyl", "alkoxyalkyl", and the like. When the term "alkyl" is used as a suffix following another term, as in "phenylalkyl", or "hydroxyalkyl", this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "spirocycloalkyl", as used herein, means a spirocyclic cycloalkyl group, such as, for example, spiro[3.3]heptane. The term spiroheterocycloalkyl, as used herein, means a spirocyclic heterocycloalkyl, such as, for example, 2,6-diaza spiro[3.3]heptane.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo-lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethylethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "PCy$_3$" refers to a phosphine trisubstituted with three cyclic moieties.

The terms "haloalkoxy" or "halo-lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The terms "alkylsulfonylamino" and "arylsulfonylamino" as used herein refers to a group of formula —NR'S(=O)$_2$R wherein R is alkyl or aryl respectively, R' is hydrogen or $C_{1-3}$ alkyl, and alkyl and aryl are as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term carboxy-alkyl as used herein refers to an alkyl moiety wherein one, hydrogen atom has been replaced with a carboxyl with the understanding that the point of attachment of the heteroalkyl radical is through a carbon atom. The term "carboxy" or "carboxyl" refers to a —CO$_2$H moiety.

The term "heteroaryl" or "heteroaromatic" as used herein means a monocyclic or bicyclic radical of 5 to 12 ring atoms having at least one aromatic or partially unsaturated ring containing four to eight atoms per ring, incorporating one or more N, O, or S heteroatoms, the remaining ring atoms being carbon, with the understanding that the attachment point of the heteroaryl radical will be on an aromatic or partially unsaturated ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, oxazinyl, pyrrolyl, pyrazolyl, imidazolyl, oxazolyl, 4,5-Dihydro-oxazolyl, 5,6-Dihydro-4H-[1,3]oxazolyl, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole, naphthyridinyl, 5,6,7,8-Tetrahydro-[1,6]naphthyridinyl, and benzisothiazole. Bicyclic moieties can be optionally substituted on either ring, however the point of attachment is on a ring containing a heteroatom.

The term "heterocyclyl", "heterocycloalkyl" or "heterocycle" as used herein denotes a monovalent saturated cyclic radical, consisting of one or more rings, preferably one to two rings, including spirocyclic ring systems, of three to eight atoms per ring, incorporating one or more ring heteroatoms (chosen from N, O or $S(O)_{0-2}$), and which can optionally be independently substituted with one or more, preferably one or two substituents selected from hydroxy, oxo, cyano, lower alkyl, lower alkoxy, lower haloalkoxy, alkylthio, halo, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and ionic forms thereof, unless otherwise indicated. Examples of heterocyclic radicals include, but are not limited to, morpholinyl, piperazinyl, piperidinyl, azetidinyl, pyrrolidinyl, hexahydroazepinyl, oxetanyl, tetrahydrofuranyl, tetrahydrothiophenyl, oxazolidinyl, thiazolidinyl, isoxazolidinyl, tetrahydropyranyl, thiomorpholinyl, quinuclidinyl and imidazolinyl, and ionic forms thereof. Examples may also be bicyclic, such as, for example, 3,8-diaza-bicyclo[3.2.1]octane, 2,5-diaza-bicyclo[2.2.2]octane, or octahydro-pyrazino[2,1-c][1,4]oxazine.

Inhibitors of Btk

The application provides a compound of Formula I,

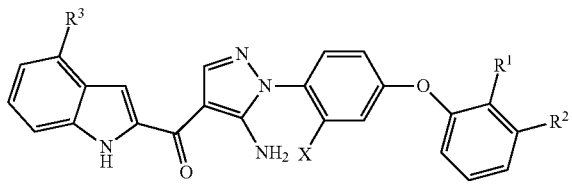

wherein:
$R^1$ is H or halo;
$R^2$ is H, halo, or cyano;
$R^3$ is $R^4$ or $R^5$;
    $R^4$ is halo or cyano;
    $R^5$ is phenyl, heteroaryl, —C(=O)$R^{5'}$, lower alkyl, or benzyl, optionally substituted with one or more $R^{5'}$;
    $R^{5'}$ is lower alkyl, cyano, hydroxyl, heterocycloalkyl, phenyl, amino, alkyl amino, dialkyl amino, or lower alkoxy; and
X is lower alkyl or halo;
or a pharmaceutically acceptable salt thereof.

The application provides a compound of Formula I, wherein X is methyl.

The application provides a compound of Formula I, wherein X is halo.

The application provides a compound of Formula I, wherein X is methyl and $R^5$ is heteroaryl, optionally substituted with one or more $R^{5'}$.

The application provides a compound of Formula I, wherein $R^5$ is thiophenyl, optionally substituted with one or more $R^{5'}$.

The application provides a compound of Formula I, wherein $R^5$ is pyridyl, optionally substituted with one or more $R^{5'}$.

The application provides any of the above compounds of Formula I, wherein $R^1$ is F and $R^2$ is F.

The application alternatively provides any of the above compounds of Formula I, wherein $R^1$ is H and $R^2$ is cyano.

The application provides a compound of Formula I, wherein $R^5$ is —C(=O)$R^{5'}$.

The application provides a compound of Formula I, wherein $R^{5'}$ is morpholinyl, piperidinyl, loweralyl piperidinyl, or lower alkoxy.

The application provides a compound of Formula I, wherein $R^1$ is F and $R^2$ is F.

The application provides a compound of Formula I, wherein $R^1$ is H and $R^2$ is cyano.

The application provides a compound of Formula I, wherein $R^5$ is phenyl or benzyl, optionally substituted with one or more $R^{5'}$.

The application provides a compound of Formula I, wherein $R^5$ is lower alkylene, optionally substituted with one or more $R^{5'}$.

The application provides either of the above compounds of Formula I, wherein $R^1$ is F and $R^2$ is F.

The application alternatively provides either of the above compounds of Formula I, wherein $R^1$ is H and $R^2$ is cyano.

The application provides a compound of Formula I, selected from the group consisting of:

{5-Amino-1-[4-(2,3-difluoro-phenoxy)-2-methyl-phenyl]-1H-pyrazol-4-yl}-(4-bromo-1H-indol-2-yl)-methanone;

{5-Amino-1-[4-(2,3-difluoro-phenoxy)-2-methyl-phenyl]-1H-pyrazol-4-yl}-(4-phenyl-1H-indol-2-yl)-methanone;

{5-Amino-1-[4-(2,3-difluoro-phenoxy)-2-methyl-phenyl]-1H-pyrazol-4-yl}-(4-thiophen-3-yl-1H-indol-2-yl)-methanone;

{5-Amino-1-[4-(2,3-difluoro-phenoxy)-2-methyl-phenyl]-1H-pyrazol-4-yl}-(4-pyrazol-1-yl-1H-indol-2-yl)-methanone;

{5-Amino-1-[4-(2,3-difluoro-phenoxy)-2-methyl-phenyl]-1H-pyrazol-4-yl}-(4-thiophen-2-yl-1H-indol-2-yl)-methanone;

{5-Amino-1-[4-(2,3-difluoro-phenoxy)-2-methyl-phenyl]-1H-pyrazol-4-yl}-[4-(morpholine-4-carbonyl)-1H-indol-2-yl]-methanone;

{5-Amino-1-[4-(2,3-difluoro-phenoxy)-2-methyl-phenyl]-1H-pyrazol-4-yl}-[4-(1-methyl-1H-pyrazol-4-yl)-1H-indol-2-yl]-methanone;

{5-Amino-1-[4-(2,3-difluoro-phenoxy)-2-methyl-phenyl]-1H-pyrazol-4-yl}-(4-pyridin-2-yl-1H-indol-2-yl)-methanone;

{5-Amino-1-[4-(2,3-difluoro-phenoxy)-2-methyl-phenyl]-1H-pyrazol-4-yl}-(4-benzyl-1H-indol-2-yl)-methanone;

{5-Amino-1-[4-(2,3-difluoro-phenoxy)-2-methyl-phenyl]-1H-pyrazol-4-yl}-[4-(1H-pyrazol-4-yl)-1H-indol-2-yl]-methanone;

3-(2-{5-Amino-1-[4-(2,3-difluoro-phenoxy)-2-methyl-phenyl]-1H-pyrazole-4-carbonyl}-1H-indol-4-yl)-benzonitrile;

{5-Amino-1-[4-(2,3-difluoro-phenoxy)-2-methyl-phenyl]-1H-pyrazol-4-yl}-[4-(3-chloro-phenyl)-1H-indol-2-yl]-methanone;

3-(2-{5-Amino-1-[4-(2,3-difluoro-phenoxy)-2-methyl-phenyl]-1H-pyrazole-4-carbonyl}-1H-indol-4-ylmethyl)-benzonitrile;

3-(4-{5-Amino-4-[4-(1H-pyrazol-4-yl)-1H-indole-2-carbonyl]-pyrazol-1-yl}-3-methyl-phenoxy)-benzonitrile;

3-(4-{5-Amino-4-[4-(morpholine-4-carbonyl)-1H-indole-2-carbonyl]-pyrazol-1-yl}-3-methyl-phenoxy)-benzonitrile;

3-(4-{5-Amino-4-[4-(4-methyl-piperazine-1-carbonyl)-1H-indole-2-carbonyl]-pyrazol-1-yl}-3-methyl-phenoxy)-benzonitrile;

3-(4-{5-Amino-4-[4-(3-methoxy-benzyl)-1H-indole-2-carbonyl]pyrazol-1-yl}-3-methyl-phenoxy)-benzonitrile;

2-{5-Amino-1-[4-(2,3-difluoro-phenoxy)-2-methyl-phenyl]-1H-pyrazole-4-carbonyl}-1H-indole-4-carboxylic acid methyl ester;

{5-Amino-1-[4-(2,3-difluoro-phenoxy)-2-methyl-phenyl]-1H-pyrazol-4-yl}-(4-morpholin-4-ylmethyl-1H-indol-2-yl)-methanone;

3-{4-[5-Amino-4-(4-cyanomethyl-1H-indole-2-carbonyl)-pyrazol-1-yl]-3-methyl-phenoxy}-benzonitrile; and 2-{5-Amino-1-[4-(3-cyano-phenoxy)-2-methyl-phenyl]-1H-pyrazole-4-carbonyl}-1H-indole-4-carboxylic acid methylamide.

The application provides a method for treating an inflammatory and/or autoimmune condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a method for treating cancer comprising administering to a patient in need thereof a therapeutically effective amount of the compound of Formula I.

The application provides a pharmaceutical composition comprising the compound of Formula I.

The application provides a pharmaceutical composition comprising the compound of Formula I, admixed with at least one pharmaceutically acceptable carrier, excipient or diluent.

The application provides the use of the compound of formula I as therapeutically active substance.

The application provides a use of the compound of formula I in the manufacture of a medicament for the treatment of an inflammatory disorder.

The application provides a use of the compound of formula I in the manufacture of a medicament for the treatment of an autoimmune disorder.

The application provides a use of the compound of formula I in the manufacture of a medicament for the treatment of rheumatoid arthritis.

The application provides a use of the compound of formula I in the manufacture of a medicament for the treatment of asthma.

The application provides the use of a compound as described above for the treatment of inflammatory and/or autoimmune condition.

The application provides the use of a compound as described above for the treatment of rheumatoid arthritis.

The application provides the use of a compound as described above for the treatment of asthma.

The application provides the use of a compound as described above for the treatment of inflammatory and/or autoimmune condition.

The application provides the use of a compound as described above for the treatment of rheumatoid arthritis.

The application provides the use of a compound as described above for the treatment of asthma.

The application provides a compound as described above for use in the treatment of inflammatory and/or autoimmune condition.

The application provides a compound as described above for use in the treatment of rheumatoid arthritis.

The application provides a compound as described above for use in the treatment of asthma.

The application provides a compound, method, or composition as described herein.

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of compounds according to generic Formula I:

TABLE I

| Compound | Nomenclature | Structure |
|---|---|---|
| 1 | {5-Amino-1-[4-(2,3-difluoro-phenoxy)-2-methyl-phenyl]-1H-pyrazol-4-yl}-(4-bromo-1H-indol-2-yl)-methanone | 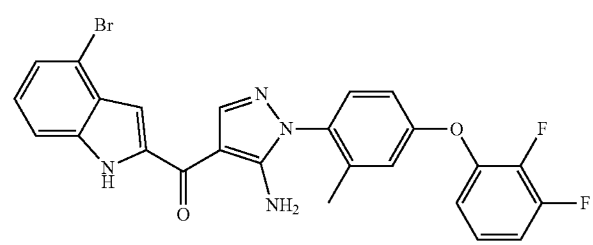 [SMILES: Cc1cc(Oc2cccc(F)c2F)ccc1-n1ncc(C(=O)c2cc3c(Br)cccc3[nH]2)c1N] |

TABLE I-continued

| Compound | Nomenclature | Structure |
|---|---|---|
| 2 | {5-Amino-1-[4-(2,3-difluoro-phenoxy)-2-methyl-phenyl]-1H-pyrazol-4-yl}-(4-phenyl-1H-indol-2-yl)-methanone | 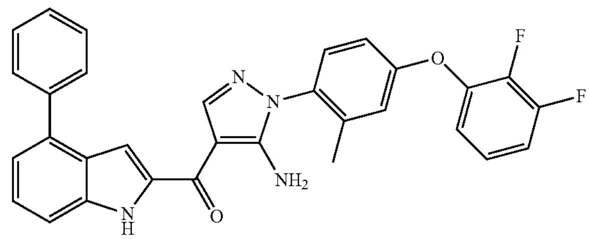 [SMILES: Cc1cc(Oc2cccc(F)c2F)ccc1-n1ncc(C(=O)c2cc3c(-c4ccccc4)cccc3[nH]2)c1N] |
| 3 | {5-Amino-1-[4-(2,3-difluoro-phenoxy)-2-methyl-phenyl]-1H-pyrazol-4-yl}-(4-thiophen-3-yl-1H-indol-2-yl)-methanone | 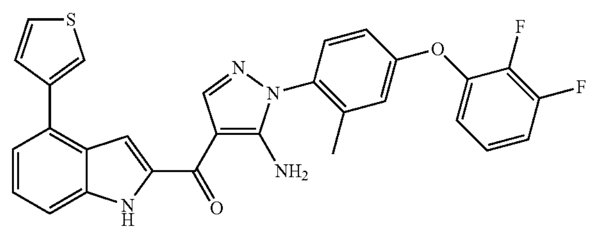 [SMILES: Cc1cc(Oc2cccc(F)c2F)ccc1-n1ncc(C(=O)c2cc3c(-c4ccsc4)cccc3[nH]2)c1N] |
| 4 | {5-Amino-1-[4-(2,3-difluoro-phenoxy)-2-methyl-phenyl]-1H-pyrazol-4-yl}-(4-pyrazol-1-yl-1H-indol-2-yl)-methanone | 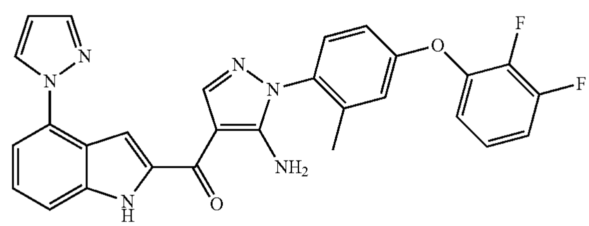 [SMILES: Cc1cc(Oc2cccc(F)c2F)ccc1-n1ncc(C(=O)c2cc3c(-n4cccn4)cccc3[nH]2)c1N] |
| 5 | {5-Amino-1-[4-(2,3-difluoro-phenoxy)-2-methyl-phenyl]-1H-pyrazol-4-yl}-(4-thiophen-2-yl-1H-indol-2-yl)-methanone | 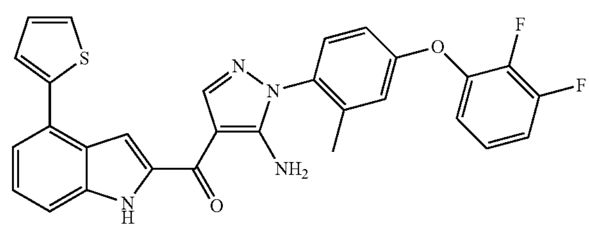 [SMILES: Cc1cc(Oc2cccc(F)c2F)ccc1-n1ncc(C(=O)c2cc3c(-c4cccs4)cccc3[nH]2)c1N] |
| 6 | {5-Amino-1-[4-(2,3-difluoro-phenoxy)-2-methyl-phenyl]-1H-pyrazol-4-yl}-[4-(morpholine-4-carbonyl)-1H-indol-2-yl]-methanone | 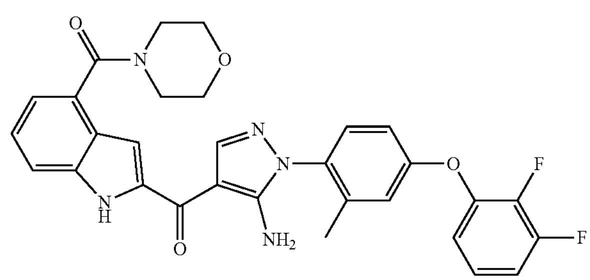 [SMILES: Cc1cc(Oc2cccc(F)c2F)ccc1-n1ncc(C(=O)c2cc3c(C(=O)N4CCOCC4)cccc3[nH]2)c1N] |
| 7 | {5-Amino-1-[4-(2,3-difluoro-phenoxy)-2-methyl-phenyl]-1H-pyrazol-4-yl}-[4-(1-methyl-1H-pyrazol-4-yl)-1H-indol-2-yl]-methanone | 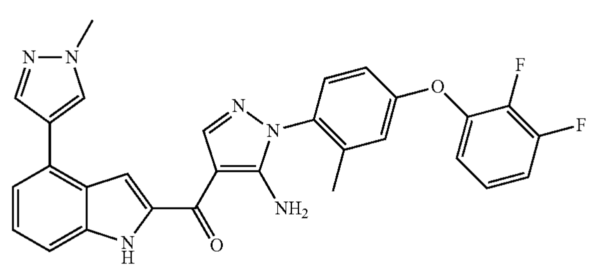 [SMILES: Cc1cc(Oc2cccc(F)c2F)ccc1-n1ncc(C(=O)c2cc3c(-c4cnn(C)c4)cccc3[nH]2)c1N] |

TABLE I-continued

| Compound | Nomenclature | Structure |
| --- | --- | --- |
| 8 | {5-Amino-1-[4-(2,3-difluoro-phenoxy)-2-methyl-phenyl]-1H-pyrazol-4-yl}-(4-pyridin-2-yl-1H-indol-2-yl)-methanone | 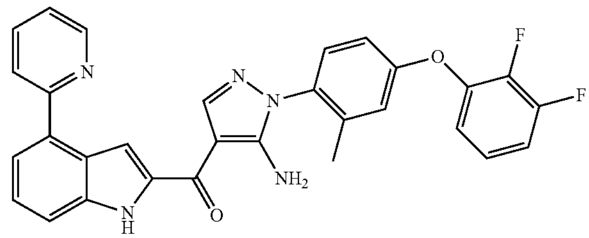 |
| 9 | {5-Amino-1-[4-(2,3-difluoro-phenoxy)-2-methyl-phenyl]-1H-pyrazol-4-yl}-(4-benzyl-1H-indol-2-yl)-methanone | 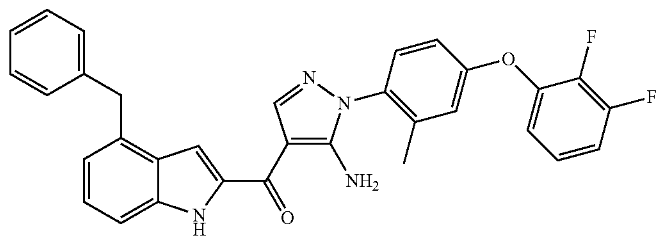 [SMILES: Cc1cc(Oc2cccc(F)c2F)ccc1-n1ncc(C(=O)c2cc3c(Cc4ccccc4)cccc3[nH]2)c1N] |
| 10 | {5-Amino-1-[4-(2,3-difluoro-phenoxy)-2-methyl-phenyl]-1H-pyrazol-4-yl}-[4-(1H-pyrazol-4-yl)-1H-indol-2-yl]-methanone | 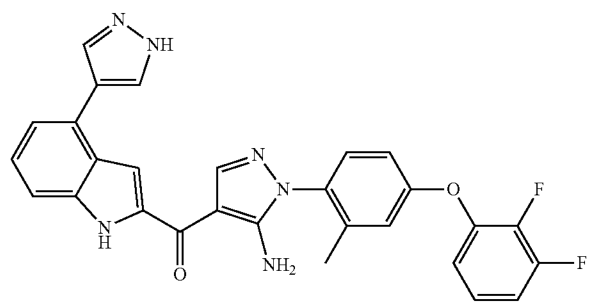 [SMILES: Cc1cc(Oc2cccc(F)c2F)ccc1-n1ncc(C(=O)c2cc3c(-c4cn[nH]c4)cccc3[nH]2)c1N] |
| 11 | 3-(2-{5-Amino-1-[4-(2,3-difluoro-phenoxy)-2-methyl-phenyl]-1H-pyrazole-4-carbonyl}-1H-indol-4-yl)-benzonitrile | 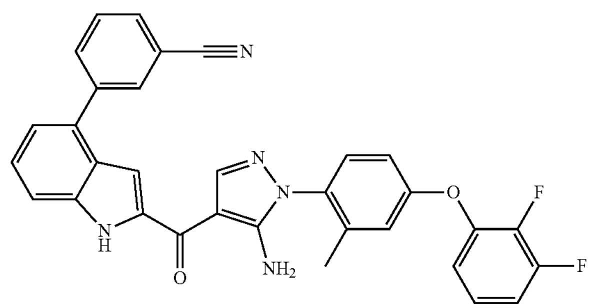 [SMILES: Cc1cc(Oc2cccc(F)c2F)ccc1-n1ncc(C(=O)c2cc3c(-c4cccc(C#N)c4)cccc3[nH]2)c1N] |
| 12 | {5-Amino-1-[4-(2,3-difluoro-phenoxy)-2-methyl-phenyl]-1H-pyrazol-4-yl}-[4-(3-chloro-phenyl)-1H-indol-2-yl]-methanone | 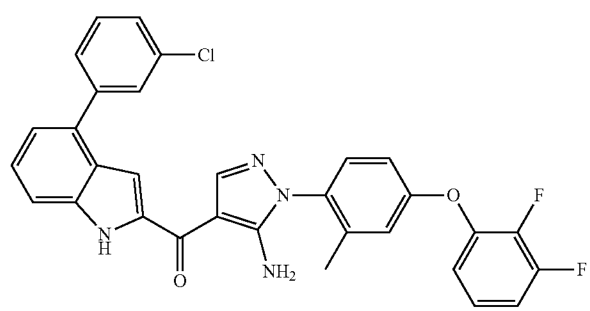 [SMILES: Cc1cc(Oc2cccc(F)c2F)ccc1-n1ncc(C(=O)c2cc3c(-c4cccc(Cl)c4)cccc3[nH]2)c1N] |

TABLE I-continued

| Compound | Nomenclature | Structure |
|---|---|---|
| 13 | 3-(2-{5-Amino-1-[4-(2,3-difluoro-phenoxy)-2-methyl-phenyl]-1H-pyrazole-4-carbonyl}-1H-indol-4-ylmethyl)-benzonitrile | 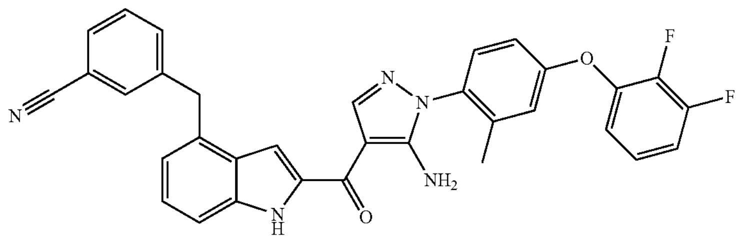 [SMILES: Cc1cc(Oc2cccc(F)c2F)ccc1-n1ncc(C(=O)c2cc3c(Cc4cccc(C#N)c4)cccc3[nH]2)c1N] |
| 14 | 3-(4-{5-Amino-4-[4-(1H-pyrazol-4-yl)-1H-indole-2-carbonyl]-pyrazol-1-yl}-3-methyl-phenoxy)-benzonitrile | 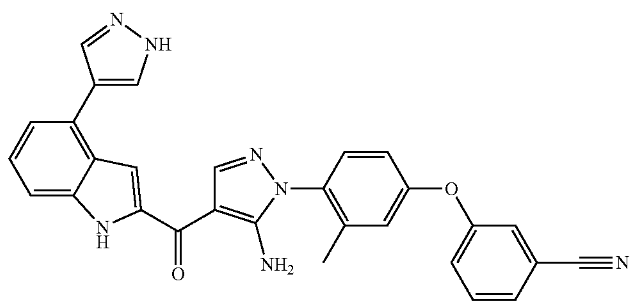 [SMILES: Cc1cc(Oc2cccc(C#N)c2)ccc1-n1ncc(C(=O)c2cc3c(-c4cn[nH]c4)cccc3[nH]2)c1N] |
| 15 | 3-(4-{5-Amino-4-[4-(morpholine-4-carbonyl)-1H-indole-2-carbonyl]-pyrazol-1-yl}-3-methyl-phenoxy)-benzonitrile | 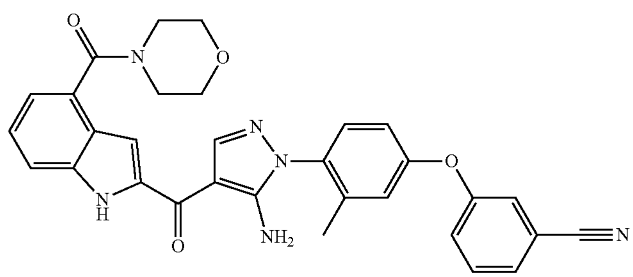 [SMILES: Cc1cc(Oc2cccc(C#N)c2)ccc1-n1ncc(C(=O)c2cc3c(C(=O)N4CCOCC4)cccc3[nH]2)c1N] |
| 16 | 3-(4-{5-Amino-4-[4-(4-methyl-piperazine-1-carbonyl)-1H-indole-2-carbonyl]-pyrazol-1-yl}-3-methyl-phenoxy)-benzonitrile | 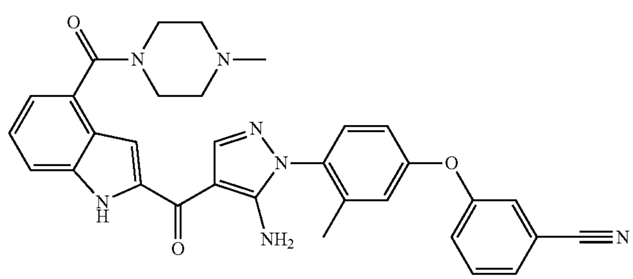 [SMILES: Cc1cc(Oc2cccc(C#N)c2)ccc1-n1ncc(C(=O)c2cc3c(C(=O)N4CCN(C)CC4)cccc3[nH]2)c1N] |
| 17 | 3-(4-{5-Amino-4-[4-(3-methoxy-benzyl)-1H-indole-2-carbonyl]-pyrazol-1-yl}-3-methyl-phenoxy)-benzonitrile | 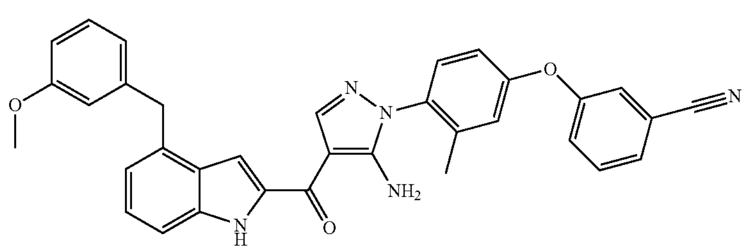 [SMILES: COc1cccc(Cc2cccc3[nH]c(C(=O)c4cnn(-c5ccc(Oc6cccc(C#N)c6)cc5C)c4N)cc23)c1] |

TABLE I-continued

| Compound | Nomenclature | Structure |
|---|---|---|
| 18 | 2-{5-Amino-1-[4-(2,3-difluoro-phenoxy)-2-methyl-phenyl]-1H-pyrazole-4-carbonyl}-1H-indole-4-carboxylic acid methyl ester | 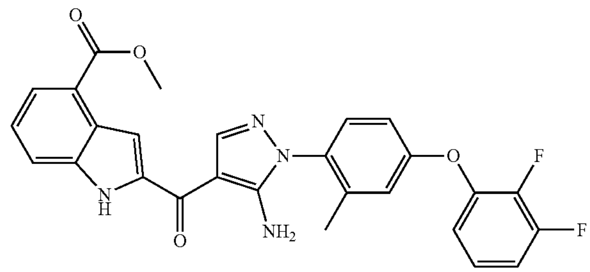 [SMILES: COC(=O)c1cccc2[nH]c(C(=O)c3cnn(-c4ccc(Oc5cccc(F)c5F)cc4C)c3N)cc12] |
| 19 | {5-Amino-1-[4-(2,3-difluoro-phenoxy)-2-methyl-phenyl]-1H-pyrazol-4-yl}-(4-morpholin-4-ylmethyl-1H-indol-2-yl)-methanone | 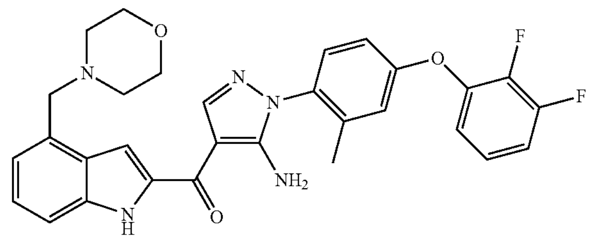 [SMILES: Cc1cc(Oc2cccc(F)c2F)ccc1-n1ncc(C(=O)c2cc3c(CN4CCOCC4)cccc3[nH]2)c1N] |
| 20 | 3-{4-[5-Amino-4-(4-cyanomethyl-1H-indole-2-carbonyl)-pyrazol-1-yl]-3-methyl-phenoxy}-benzonitrile | 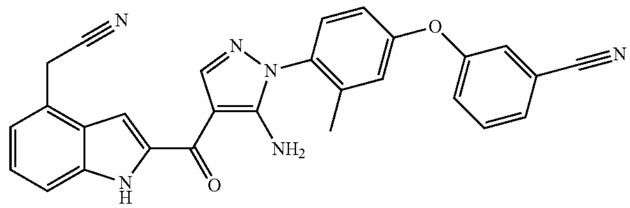 [SMILES: Cc1cc(Oc2cccc(C#N)c2)ccc1-n1ncc(C(=O)c2cc3c(CC#N)cccc3[nH]2)c1N] |
| 21 | 2-{5-Amino-1-[4-(3-cyano-phenoxy)-2-methyl-phenyl]-1H-pyrazole-4-carbonyl}-1H-indole-4-carboxylic acid methylamide | 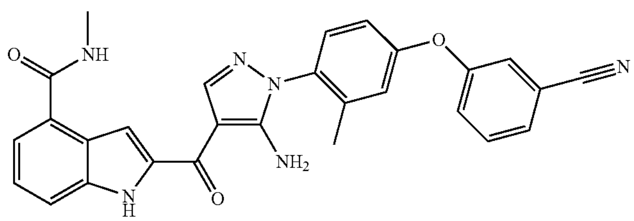 [SMILES: CNC(=O)c1cccc2[nH]c(C(=O)c3cnn(-c4ccc(Oc5cccc(C#N)c5)cc4C)c3N)cc12] |

General Synthetic Schemes

The compounds of the present invention may be prepared by any conventional means. Suitable processes for synthesizing these compounds are provided in the examples. Generally, compounds of the invention may be prepared according to the schemes below.

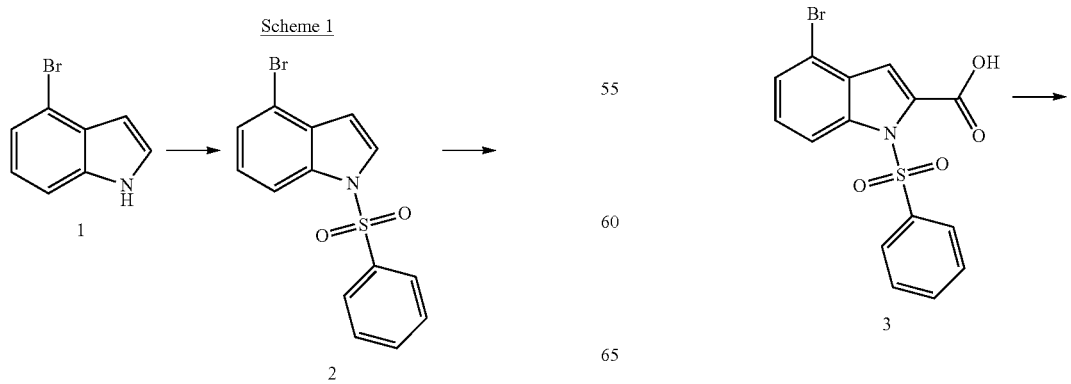

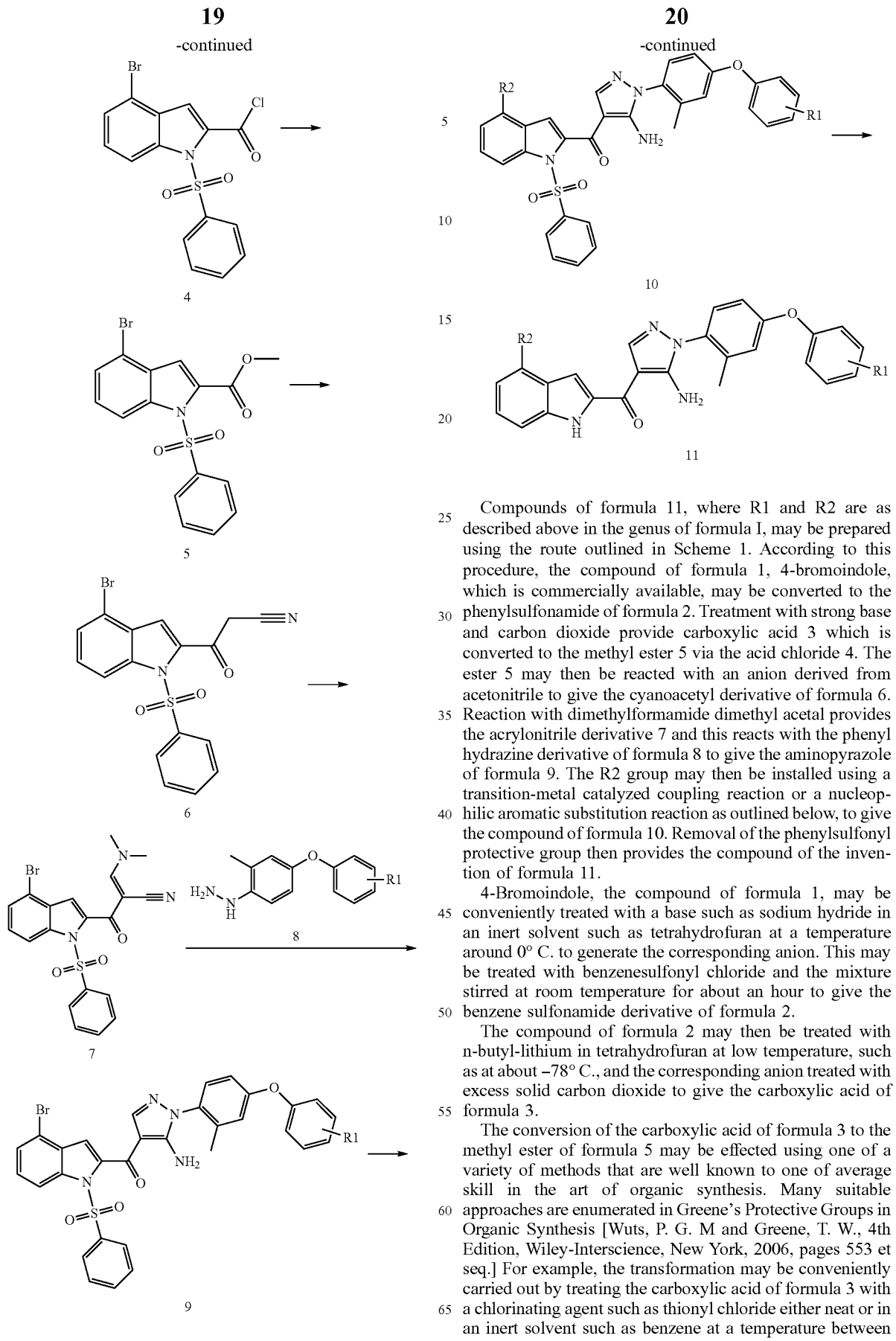

Compounds of formula 11, where R1 and R2 are as described above in the genus of formula I, may be prepared using the route outlined in Scheme 1. According to this procedure, the compound of formula 1, 4-bromoindole, which is commercially available, may be converted to the phenylsulfonamide of formula 2. Treatment with strong base and carbon dioxide provide carboxylic acid 3 which is converted to the methyl ester 5 via the acid chloride 4. The ester 5 may then be reacted with an anion derived from acetonitrile to give the cyanoacetyl derivative of formula 6. Reaction with dimethylformamide dimethyl acetal provides the acrylonitrile derivative 7 and this reacts with the phenyl hydrazine derivative of formula 8 to give the aminopyrazole of formula 9. The R2 group may then be installed using a transition-metal catalyzed coupling reaction or a nucleophilic aromatic substitution reaction as outlined below, to give the compound of formula 10. Removal of the phenylsulfonyl protective group then provides the compound of the invention of formula 11.

4-Bromoindole, the compound of formula 1, may be conveniently treated with a base such as sodium hydride in an inert solvent such as tetrahydrofuran at a temperature around 0° C. to generate the corresponding anion. This may be treated with benzenesulfonyl chloride and the mixture stirred at room temperature for about an hour to give the benzene sulfonamide derivative of formula 2.

The compound of formula 2 may then be treated with n-butyl-lithium in tetrahydrofuran at low temperature, such as at about −78° C., and the corresponding anion treated with excess solid carbon dioxide to give the carboxylic acid of formula 3.

The conversion of the carboxylic acid of formula 3 to the methyl ester of formula 5 may be effected using one of a variety of methods that are well known to one of average skill in the art of organic synthesis. Many suitable approaches are enumerated in Greene's Protective Groups in Organic Synthesis [Wuts, P. G. M and Greene, T. W., 4th Edition, Wiley-Interscience, New York, 2006, pages 553 et seq.] For example, the transformation may be conveniently carried out by treating the carboxylic acid of formula 3 with a chlorinating agent such as thionyl chloride either neat or in an inert solvent such as benzene at a temperature between about 50° C. and about the reflux temperature. The resulting acid chloride of formula 4 may then be treated with methanol in the presence of a base such as triethylamine or diisopropylethylamine or pyridine either using methanol as solvent or in an inert solvent such as tetrahydrofuran at about room temperature.

Specific conditions for the preparation of the compound of formula 5 may be found in the literature, in Mahboobi, S. et al. *J. Med. Chem.* 2006, 49, 3101-3115.

The compound of formula 5 may be conveniently converted to the cyanoacetyl derivative of formula 6 by treating it with a mixture of acetonitrile and a strong base such as lithium diisopropylamide or lithium hexamethyldisilazide in a solvent such as tetrahydrofuran at low temperature, such as at about −78° C. Conditions for such a reaction may be found in the patent literature, for example in Taka, N. et al. US 20120208811 Page 163.

The compound of formula 6 may be converted to the acrylonitrile derivative of formula 7 by treatment with N,N-dimethylformamide dimethyl acetal in an inert solvent such as an aromatic hydrocarbon (e.g., toluene) or tetrahydrofuran at about room temperature. Conditions for such a reaction may be found in the patent literature, for example in Taka, N. et al. US 20120208811 page 132.

The acrylonitrile derivative of formula 7 may be converted to the aminopyrazole derivative of formula 9 by treatment with an intermediate of formula 8, where R1 is as described above in the genus of formula I, in an alcoholic solvent such as methanol or ethanol or isopropanol, at about the reflux temperature of the solvent. Conditions for such a reaction may be found in the patent literature, for example in Taka, N. et al. US 20120208811 Page 94.

The reaction of a compound of formula 9 with a compound of formula $R_2$—X, where X represents boronic acid, boronate ester, potassium trifluoroborate, trimethyltin or tri-n-butyl-tin, to give a compound of formula 10 can be effected using Suzuki or Stille or Negishi coupling conditions which are well known to one of average skill in the art. For example, in a Suzuki reaction, the reaction can be conveniently carried out by reacting a compound of formula 9 with a compound of formula $R_2$—B(OH)$_2$, in a convenient inert solvent such as a polar aprotic solvent (e.g., N,N-dimethylformamide) or an ether (e.g., dioxane) or water, or indeed in a mixture of such solvents, in the presence of a catalytic amount of a palladium(0) precursor (for example, palladium(II) acetate or bis(triphenylphosphine)palladium (II) chloride), in the optional additional presence of a catalytic amount of a phosphine ligand, for example tri-o-tolylphosphine or tri-tert-butylphosphine, or alternatively in the presence of a preformed complex of palladium(0) with a phosphine ligand such as bis(tri-cyclohexylphosphine) palladium, tetrakis(triphenylphosphine)-palladium(0) or [1,1-bis(diphenylphosphino)ferrocene]dichloropalladium (II)), and also in the presence of an inorganic base, for example, an alkali metal carbonate, bicarbonate or phosphate (e.g., potassium phosphate or sodium carbonate) at a temperature between about room temperature and about 100 degrees, and preferably between about room temperature and about 50 degrees. The Suzuki reaction is familiar to one of ordinary skill in the art of organic synthesis, and has been reviewed several times, notably in Miyaura, N.; Suzuki, A. *Chem. Rev.* 1995, 95, 2457-2483 and, more recently, in Alonso, F.; Beletskaya, I. P.; Yus, M. *Tetrahedron* 2008, 64, 3047-3101. Examples of specific conditions useful for Suzuki coupling may be found in many references in the literature including: Tiede, S. et al. *Angew. Chem. Intl. Edn.* 2010, 49, 3972-3975; Schmidt, A. and Rahimi, A. *Chem. Commun.* 2010, 46, 2995-2997; Lee, S. H. et al. US 20100063281; and Tobisu, M. et al. *J. Org. Chem.* 2010, 75, 4835-4840 (Supporting Information). Stille coupling is well known to one of average skill in the field of organic synthesis, and may be used as an alternative to the Suzuki coupling, examples of conditions for which have been provided above. Stille coupling has been reviewed, including in Farina, V. et al. *Org. Reactions* 1997, 50, 1-652. Examples of specific conditions that have been used for Stille coupling may be found in the literature, for example in Littke, A. F. et al. *J. Am. Chem. Soc.* 2002, 124, 5343-6348; in Alberati-Giani, D. et al. U.S. Pat. No. 7,462,617; and in Robl, J. A. U.S. Pat. No. 5,072,023. For example, the reaction may be carried out by treating the compound of formula 9 with a compound of formula $R_2$—SnA$_3$, where A represents a lower alkyl group such as methyl or n-butyl, in a convenient inert solvent such as a polar aprotic solvent (e.g., N,N-dimethylformamide) or an aromatic hydrocarbon (e.g., toluene) or acetonitrile or dimethoxyethane, in the presence of a catalytic amount of a palladium catalyst such as tetrakis(triphenylphosphine)palladium(0) or bis(triphenylphosphine)palladium(II) chloride or bis(acetato)bis(triphenylphosphine)palladium(0) or tris(dibenzylideneacetone)dipalladium(0) at a temperature between about 80° C. and about 180° C.

Compounds of formula 10 in which R2 represents a carboxamide or ester functionality with the carbonyl carbon attached to the indole ring may be conveniently prepared using a transition metal-catalyzed carbonylative coupling reaction. According to this process, the compound of formula 9 is heated with an amine (to give a carboxamide product) or a lower alcohol (to give a carboxylate ester product) in the presence of carbon monoxide gas and a catalytic amount of a palladium catalyst such as tetrakis (triphenylphosphine)palladium(0) or a combination of a palladium catalyst such as bis(benzonitrile)palladium(II) dichloride with a ligand such as 1,1'-bis(diphenylphosphino) ferrocene in a solvent such as tetrahydrofuran or toluene in a sealed tube at a temperature between about 80° C. and about 100° C. Examples for specific conditions that may be used for such a reaction may be found in the literature, for example in Kumar, K. et al. *Org. Letters* 2004, 6, 7-10.

Compounds of formula 10 in which R2 represents an aralkyl group such as a benzyl group or a substituted benzyl group may be conveniently prepared using a transition metal-catalyzed coupling reaction such as a Negishi reaction. According to this process, the compound of formula 9 is heated with an aralkylzinc reagent in the presence of a catalytic amount of a palladium catalyst such as palladium (II) acetate with a ligand such as 2-dicyclohexylphosphino-2',6'-dimethoxybiphenyl (S-Phos) or using tetrakis(triphenylphosphine)-palladium(0) in a solvent such as tetrahydrofuran or toluene at a temperature between about 50° C. and about 90° C. Examples for specific conditions that may be used for such a reaction may be found in the literature, for example in Ellsworth, B. A. et al. US 20110082165 page 51.

Compounds of formula 10 in which R2 represents a cyanomethyl group may be conveniently prepared using a transition metal-catalyzed coupling reaction with tributylstannanyl-acetonitrile or a lower alkyl cyanoacetate. The reaction with tributylstannanyl-acetonitrile may be carried out by treating the compound of formula 9 with tributylstannanyl-acetonitrile in the presence of a palladium catalyst such as bis(triphenylphosphino)palladium(II) dichloride or bis(tri-o-tolylphosphino)palladium(II) dichloride in toluene or xylene at a temperature between about 110° C. and about 130° C. Conditions for such as reaction may be found in the literature, for example in Ettaoussi, M. et al. *Eur. J. Med. Chem.* 2012, 49, 310-323 and in Song, D. et al. WO 2011117211 page 118. The reaction with a lower alkyl cyanoacetate may be carried out by treating the compound of formula 9 with the lower alkyl cyanoacetate in the presence of a palladium catalyst such as bis(tri-tert-butylphosphine)palladium(0), or a mixture of a palladium catalyst such as tris-(dibenzylideneacetone)dipalladium(0) or bis(dibenzylideneacetone)palladium(0) and a ligand such as tert-butylphosphine, and a base such as trisodium phosphate in a solvent such as toluene in a sealed tube at a temperature between about 70° C. and about 100° C. In the case where the lower alkyl cyanoacetate is tert-butyl cyanoacetate, the tert-butyl group may undergo a decarboxylation reaction under the reaction conditions to give the desired compound of formula 10 where R2 represents a cyanomethyl group. In the case where the lower alkyl cyanoacetate is methyl cyanoacetate or ethyl cyanoacetate, an additional hydrolysis step is required and this is conveniently affected by heating the product of the palladium-catalyzed coupling with 3 M hydrochloric acid in dimethylsulfoxide at about 70° C. for several hours. Examples of conditions that may be used for such a reaction can be found in the literature, for example in Alargova, R. G. et al. US 20120015999 page 10.

The conversion of the compound of formula 10 to the compound of the invention of formula 11 may be effected using any conventional procedure. For example, the reaction may be carried out by treating the compound of formula 10 with a mixture of a base such as cesium carbonate and a lower alcohol such as methanol in a solvent such a tetrahydrofuran at a temperature between about room temperature and about the reflux temperature of the mixture. Examples of conditions that may be used for such a reaction can be found in the literature, for example in Zhang, B and Wee. A. G. H. *Org. Biomol. Chem.* 2012, 10, 4597-4608 Supplementary Information; in Alam, M. et al. US 20110071150 page 54; and in Taka, N. et al. US 20120208811 Page 55.

Scheme 2

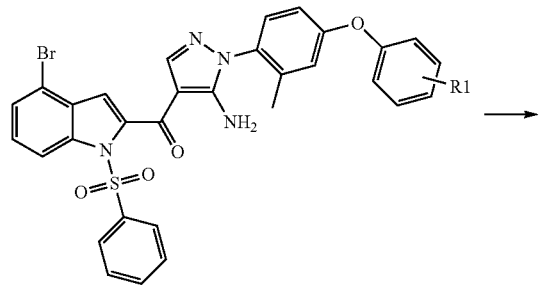

9

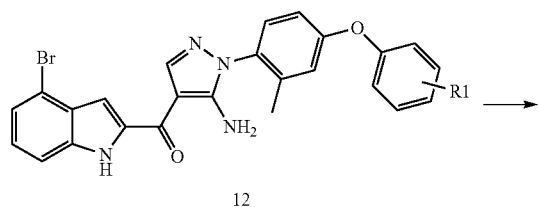

12

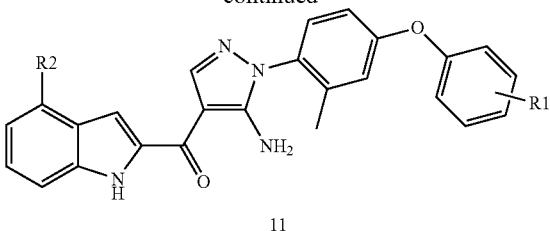

11

It will be readily apparent to one of average skill in the art of organic synthesis that, as outlined in Scheme 2, many compounds of formula 11 are also readily accessible if the protective group is removed from the compound of formula 9 rather than from the compound of formula 10.

According to this process, the deprotection reaction may be carried out by treating the compound of formula 9 with a mixture of a base such as cesium carbonate and a lower alcohol such as methanol in a solvent such a tetrahydrofuran at a temperature between about room temperature and about the reflux temperature of the mixture. Examples of conditions that may be used for such a reaction can be found in the literature, for example in Zhang, B and Wee. A. G. H. *Org. Biomol. Chem.* 2012, 10, 4597-4608 Supplementary Information; in Alam, M. et al. US 20110071150 page 54; and in Taka, N. et al. US 20120208811 Page 55.

The resulting compound of formula 12 may then be treated with a compound of formula $R_2$—$B(OH)_2$, under the conditions described above for the Suzuki reaction of the compound of formula 9 to give the desired compound of formula 11.

Compounds of formula 11 in which R2 represents an N-linked heterocycle, such as pyrazol-1-yl may also be conveniently prepared using Scheme 2. According to this process, the compound of formula 12 is treated with the N-linked heterocycle, such as pyrazole, in the presence of a base such as potassium carbonate, in the presence of a copper catalyst such as copper(I) iodide and in the presence of L-proline, in an inert solvent such as dimethylsulfoxide at a temperature between about 100° C. and about 130° C. Examples of conditions that may be used for such a reaction can be found in the literature, for example in Sun, X. et al. *Bioorg. Med. Chem. Lett.* 2011, 21, 3671-3675 Supplemental Information; and in Yokotani, J. et al. US 20110275797 page 31.

Scheme 3

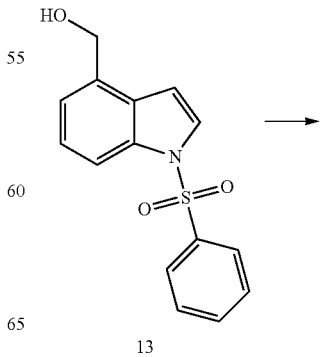

13

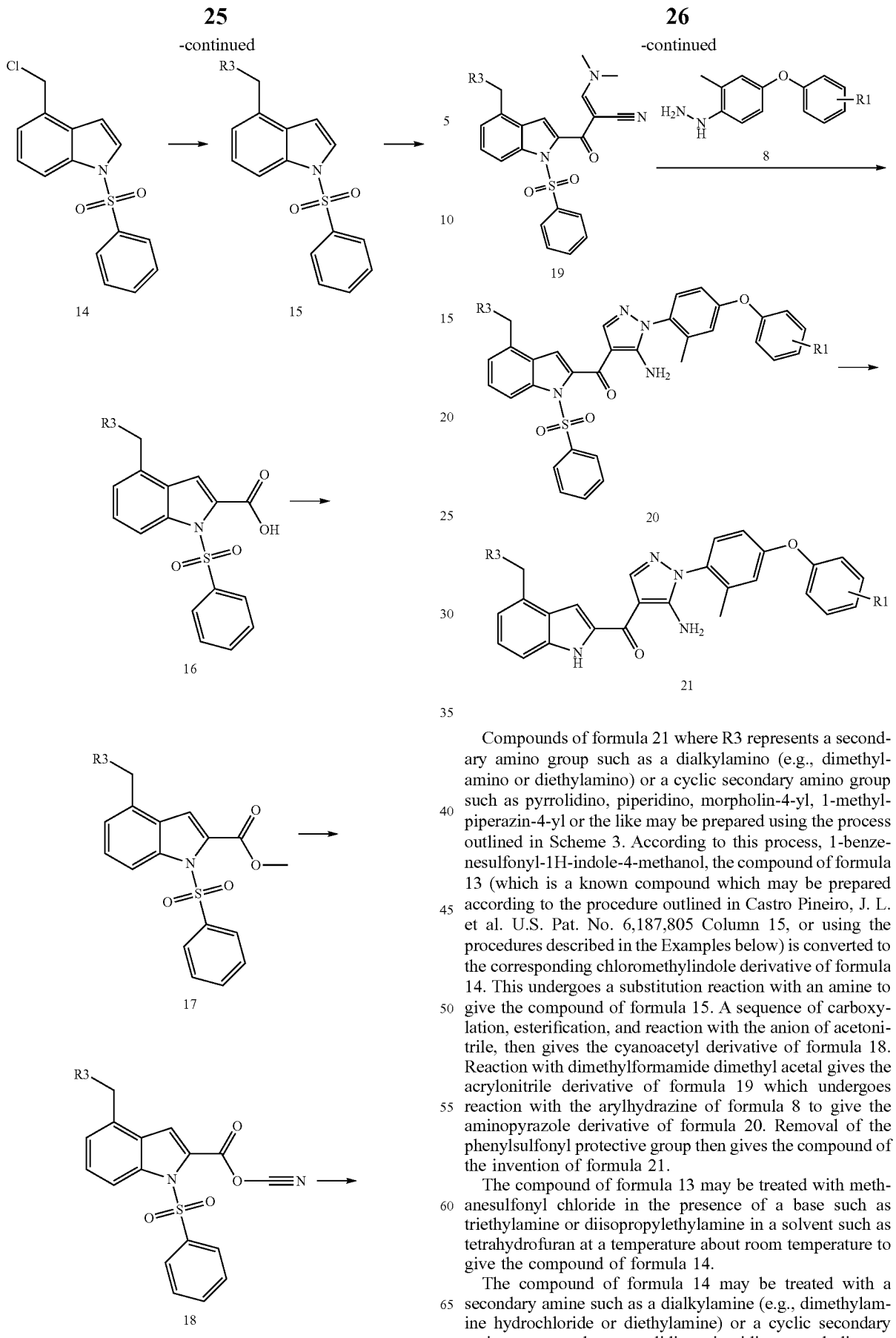

Compounds of formula 21 where R3 represents a secondary amino group such as a dialkylamino (e.g., dimethylamino or diethylamino) or a cyclic secondary amino group such as pyrrolidino, piperidino, morpholin-4-yl, 1-methylpiperazin-4-yl or the like may be prepared using the process outlined in Scheme 3. According to this process, 1-benzenesulfonyl-1H-indole-4-methanol, the compound of formula 13 (which is a known compound which may be prepared according to the procedure outlined in Castro Pineiro, J. L. et al. U.S. Pat. No. 6,187,805 Column 15, or using the procedures described in the Examples below) is converted to the corresponding chloromethylindole derivative of formula 14. This undergoes a substitution reaction with an amine to give the compound of formula 15. A sequence of carboxylation, esterification, and reaction with the anion of acetonitrile, then gives the cyanoacetyl derivative of formula 18. Reaction with dimethylformamide dimethyl acetal gives the acrylonitrile derivative of formula 19 which undergoes reaction with the arylhydrazine of formula 8 to give the aminopyrazole derivative of formula 20. Removal of the phenylsulfonyl protective group then gives the compound of the invention of formula 21.

The compound of formula 13 may be treated with methanesulfonyl chloride in the presence of a base such as triethylamine or diisopropylethylamine in a solvent such as tetrahydrofuran at a temperature about room temperature to give the compound of formula 14.

The compound of formula 14 may be treated with a secondary amine such as a dialkylamine (e.g., dimethylamine hydrochloride or diethylamine) or a cyclic secondary amino group such as pyrrolidine, piperidine, morpholine, or 1-methyl-piperazine, in the presence of an inorganic base such as potassium carbonate or cesium carbonate in an inert solvent such as acetonitrile at a temperature between about 50° C. and about 80° C. to give the amine of formula 15.

The compound of formula 15 may then be treated with a strong base such as lithium diisopropylamide or lithium hexamethyldisilazide in tetrahydrofuran at low temperature, such as at about −78° C., and the corresponding anion treated with excess solid carbon dioxide to give the carboxylic acid of formula 16.

The conversion of the carboxylic acid of formula 16 to the methyl ester of formula 17 may be effected using one of a variety of methods that are well known to one of average skill in the art of organic synthesis. Many suitable approaches are enumerated in Greene's Protective Groups in Organic Synthesis [Wuts, P. G. M and Greene, T. W., 4th Edition, Wiley-Interscience, New York, 2006, pages 553 et seq.] For example, the transformation may be conveniently carried out by treating the carboxylic acid of formula 16 with a chlorinating agent such as thionyl chloride either neat or in an inert solvent such as benzene at a temperature between about 50° C. and about the reflux temperature. The resulting acid chloride may then be treated with methanol in the presence of a base such as triethylamine or diisopropylethylamine or pyridine either using methanol as solvent or in an inert solvent such as tetrahydrofuran at about room temperature to give the ester of formula 17.

The compound of formula 17 may be conveniently converted to the cyanoacetyl derivative of formula 18 by treating it with a mixture of acetonitrile and a strong base such as lithium diisopropylamide or lithium hexamethyldisilazide in a solvent such as tetrahydrofuran at low temperature, such as at about −78° C. Conditions for such a reaction may be found in the patent literature, for example in Taka, N. et al. US 20120208811 Page 163.

The compound of formula 18 may be converted to the acrylonitrile derivative of formula 19 by treatment with N,N-dimethylformamide dimethyl acetal in an inert solvent such as an aromatic hydrocarbon (e.g., toluene) or tetrahydrofuran at about room temperature. Conditions for such a reaction may be found in the patent literature, for example in Taka, N. et al. US 20120208811 page 163.

The acrylonitrile derivative of formula 19 may be converted to the aminopyrazole derivative of formula 20 by treatment with an intermediate of formula 8, where R1 is as described above in the genus of formula I, in an alcoholic solvent such as methanol or ethanol or isopropanol, at about the reflux temperature of the solvent. Conditions for such a reaction may be found in the patent literature, for example in Taka, N. et al. US 20120208811 Page 94.

The conversion of the compound of formula 20 to the compound of the invention of formula 21 may be effected using any conventional procedure. For example, the reaction may be carried out by treating the compound of formula 20 with a mixture of a base such as cesium carbonate and a lower alcohol such as methanol in a solvent such a tetrahydrofuran at a temperature between about room temperature and about the reflux temperature of the mixture. Examples of conditions that may be used for such a reaction can be found in the literature, for example in Zhang, B and Wee. A. G. H. *Org. Biomol. Chem.* 2012, 10, 4597-4608 Supplementary Information; in Alam, M. et al. US 20110071150 page 54; and in Taka, N. et al. US 20120208811 Page 55.

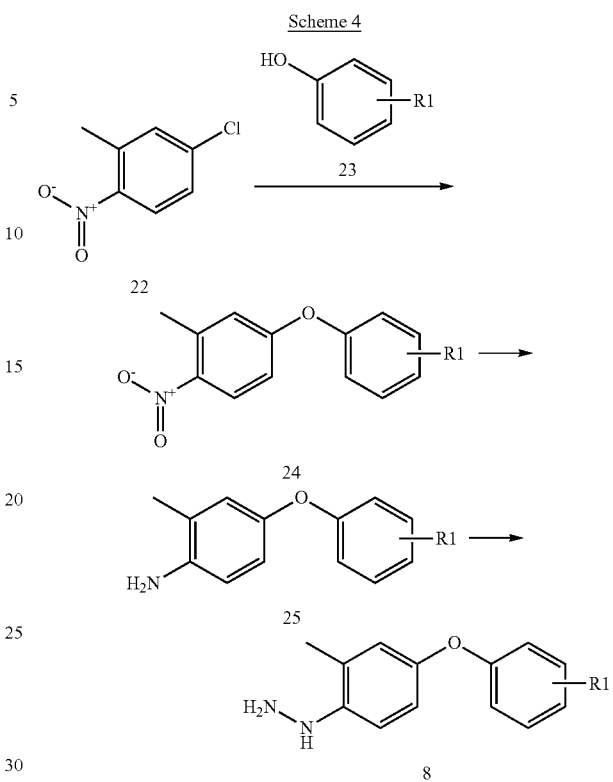

Intermediates of formula 8 where R1 is as described above in the genus of formula I, may be prepared according to scheme 4. The compound of formula 22, 4-chloro-2-methyl-1-nitro-benzene undergoes a nucleophilic aromatic substitution reaction with a phenol derivative of formula 23 to give a compound of formula 24. Reduction of the nitro group in the compound of formula 24, followed by diazotization and reduction gives the aryl-hydrazine derivative of formula 8.

4-Chloro-2-methyl-1-nitro-benzene (22) may be treated with a phenol of formula 23 in the presence of a base such as potassium carbonate or cesium carbonate in an inert solvent such as dimethylformamide at a temperature between about 100° C. and about 150° C., optionally under microwave irradiation, to give a nitro compound of formula 24. Examples of particular conditions that may be used for such a reaction may be found in the literature, for example in Chee, G.-L et al. US 20040266738 Page 5; and in Cui, S.-L. et al. *Synlett* 2004, 1829-1831.

The reduction of the nitro group in the compound of formula 24 can be effected using a variety of procedures well known to one of average skill in the field of organic synthesis. Many of these procedures are outlined in Larock, R. C. *Comprehensive Organic Transformations* John Wiley & Sons Inc. NY 1999, pp. 823 et seq. One convenient approach is to treat the compound of formula 24 with hydrogen gas in the presence of a noble metal catalyst such as palladium-on-carbon in a solvent such an alcohol (e.g., methanol or ethanol) at a pressure between about one atmosphere of hydrogen and about three atmospheres of hydrogen at about room temperature. Examples of particular conditions that may be used for such a reaction may be found in the literature, for example in Chee, G.-L et al. US 20040266738 Page 5; and in Schoenafinger, K. et al. US 20030236288 Page 18.

The diazotization and reduction of the aniline group in the compound of formula 25 may be carried out using any conventional procedure. For example, the reaction is conveniently carried out by treating the compound of formula 25 with sodium nitrite in aqueous solution in the presence of an inorganic acid such as hydrochloric acid at a temperature below about 5° C. and preferably below about 0° C., followed by the addition of a reducing agent such as tin(II) chloride or sodium dithionite at about the same temperature. Examples of particular conditions that may be used for such a reaction may be found in the literature, for example in Wipf, P. and Qiming, J. WO 2012078859 page 47; in Rewolinski, M. V. et al. WO 2009055721 page 82; and in Schoenafinger, K. et al. US 20030236288 page 18.

Pharmaceutical Compositions and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Indications and Methods of Treatment

The compounds of generic Formula I inhibit Bruton's tyrosine kinase (Btk). Activation of Btk by upstream kinases results in activation of phospholipase-Cγ which, in turn, stimulates release of pro-inflammatory mediators. Compounds of Formula I are useful in the treatment of arthritis and other anti-inflammatory and auto-immune diseases. Compounds according to Formula I are, accordingly, useful for the treatment of arthritis. Compounds of Formula I are useful for inhibiting Btk in cells and for modulating B-cell development. The present invention further comprises pharmaceutical compositions containing compounds of Formula I admixed with pharmaceutically acceptable carrier, excipients or diluents.

The compounds described herein are kinase inhibitors, in particular Btk inhibitors. These inhibitors can be useful for treating one or more diseases responsive to kinase inhibition, including diseases responsive to Btk inhibition and/or inhibition of B-cell proliferation, in mammals. Without wishing to be bound to any particular theory, it is believed that the interaction of the compounds of the invention with Btk results in the inhibition of Btk activity and thus in the pharmaceutical utility of these compounds. Accordingly, the invention includes a method of treating a mammal, for instance a human, having a disease responsive to inhibition of Btk activity, and/or inhibiting B-cell proliferation, comprising administrating to the mammal having such a disease, an effective amount of at least one chemical entity provided herein. An effective concentration may be ascertained experimentally, for example by assaying blood concentration of the compound, or theoretically, by calculating bioavailability. Other kinases that may be affected in addition to Btk include, but are not limited to, other tyrosine kinases and serine/threonine kinases.

Kinases play notable roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

An embodiment includes a method of treating a patient having an autoimmune and/or inflammatory disease, or an acute inflammatory reaction responsive to inhibition of Btk activity and/or B-cell proliferation.

Autoimmune and/or inflammatory diseases that can be affected using compounds and compositions according to the invention include, but are not limited to: psoriasis, allergy, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, and myasthenia gravis.

Included herein are methods of treatment in which at least one chemical entity provided herein is administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., *J. Biol. Chem.* 1998, 274, 1646-1656).

It has also been discovered that BTK inhibitors are useful as chemosensitizing agents, and, thus, are useful in combination with other chemotherapeutic drugs, in particular, drugs that induce apoptosis. Examples of other chemotherapeutic drugs that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Btk activity has also been associated with some leukemias expressing the bcr-abl fusion gene resulting from translocation of parts of chromosome 9 and 22. This abnormality is commonly observed in chronic myelogenous leukemia. Btk is constitutively phosphorylated by the bcr-abl kinase which initiates downstream survival signals which circumvents apoptosis in bcr-abl cells. (N. Feldhahn et al. *J. Exp. Med.* 2005 201(11):1837-1852).

Methods of Treatment

The application provides a method for treating an inflammatory and/or autoimmune condition comprising administering to a patient in need thereof a therapeutically effective amount of the compound of Formula I.

The application provides a method for treating an inflammatory condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of Formula I.

The application provides a method for treating an inflammatory and/or autoimmune condition comprising administering to a patient in need thereof a therapeutically effective amount of the Btk inhibitor compound of Formulae I.

The application provides a method for treating arthritis comprising co-administering to a patient in need thereof a therapeutically effective amount of the Btk inhibitor compound of Formula I.

The application provides a method for treating asthma comprising administering to a patient in need thereof a therapeutically effective amount of the Btk inhibitor compound of Formula I.

The application provides a method for treating cancer comprising administering to a patient in need thereof a therapeutically effective amount of the Btk inhibitor compound of Formula I.

The application provides a method of inhibiting B-cell proliferation comprising administering to a patient in need thereof a therapeutically effective amount of the Btk inhibitor compound of Formula I.

The application provides a method for inhibiting Btk activity comprising administering the Btk inhibitor compound of any one of Formula I, wherein the Btk inhibitor compound exhibits an $IC_{50}$ of 50 micromolar or less in an in vitro biochemical assay of Btk activity.

In one variation of the above method, the Btk inhibitor compound exhibits an $IC_{50}$ of 100 nanomolar or less in an in vitro biochemical assay of Btk activity.

In another variation of the above method, the compound exhibits an $IC_{50}$ of 10 nanomolar or less in an in vitro biochemical assay of Btk activity.

The application provides a method for treating an inflammatory condition comprising co-administering to a patient in need thereof a therapeutically effective amount of an anti-inflammatory compound in combination with the Btk inhibitor compound of Formula I.

The application provides a method for treating arthritis comprising co-administering to a patient in need thereof a therapeutically effective amount of an anti-inflammatory compound in combination with the Btk inhibitor compound of Formula I.

The application provides a method for treating a lymphoma or a BCR-ABL1$^+$ leukemia cells by administering to a patient in need thereof a therapeutically effective amount of the Btk inhibitor compound of Formula I.

EXAMPLES

General Abbreviations

Commonly used abbreviations include: acetyl (Ac), azo-bis-isobutyrylnitrile (AIBN), atmospheres (Atm), 9-borabicyclo[3.3.1]nonane (9-BBN or BBN), 2,2'-bis(diphenylphosphino)-1,1'-binaphthyl (BINAP), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether (Et$_2$O), ethyl isopropyl ether (EtOiPr), O-(7-azabenzotriazol-1-yl)-N, N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropylmagnesium chloride (iPrMgCl), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bis-diphenylphosphino)ferrocenyl) palladium(II) ($Pd(dppf)Cl_2$), palladium(II) acetate ($Pd(OAc)_2$), tris(dibenzylideneacetone)dipalladium(0) ($Pd_2(dba)_3$), pyridinium dichromate (PDC), phenyl (Ph), propyl (Pr), isopropyl (i-Pr), pounds per square inch (psi), pyridine (pyr), 1,2,3,4,5-Pentaphenyl-1'-(di-tert-butylphosphino)ferrocene (Q-Phos), room temperature (ambient temperature, rt or RT), sec-Butyllithium (sBuLi), tert-butyldimethylsilyl or t-BuMe$_2$Si (TBDMS), tetra-n-butylammonium fluoride (TBAF), triethylamine (TEA or Et$_3$N), 2,2,6,6-tetramethylpiperidine 1-oxyl (TEMPO), trimethylsilylethoxymethyl (SEM), triflate or $CF_3SO_2$-(Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), and N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

General Conditions

Compounds of the present invention can be prepared beginning with the commercially available starting materials by utilizing general synthetic techniques and procedures known to those skilled in the art. Outlines below are reaction schemes suitable for preparing such compounds. Further exemplification can be found in the specific examples.

Preparative Examples

Specific Abbreviations

CDCl$_3$ Deuterated chloroform
CH$_2$Cl$_2$ Dichloromethane
CH$_3$CN Acetonitrile
CO$_2$ Carbon dioxide
Conc Concentrated
Cs$_2$CO$_3$ Cesium carbonate
DIPEA Diisopropylethylamine
DMF N,N-Dimethylformamide
DMSO Dimethylsulfoxide
EtOAc Ethyl acetate
EtOH Ethanol
HCl Hydrochloric acid
K$_2$CO$_3$ Potassium carbonate
LDA Lithium diisopropylamide
LiAlH$_4$ Lithium aluminum hydride
MeOH Methanol
NaBH$_4$ Sodium borohydride
NaOH Sodium hydroxide
Na$_2$SO$_4$ Sodium sulfate
NaH Sodium hydride
NaNO$_2$ Sodium nitrite
Pd(OAc)$_2$ Palladium(II) acetate
Pd(PPh$_3$)$_4$ Tetrakis(triphenylphosphine)palladium(0)
SOCl$_2$ Thionyl chloride
THF Tetrahydrofuran
General Experimental Details Reagents were purchased from Aldrich, Oakwood, Matrix or other suppliers and used without further purification. Reactions using microwave irradiation for heating were conducted using either a Personal Chemistry Emrys Optimizer System or a CEM Discovery System. The purification of multi-milligram to multi-gram scale was conducted by methods known know to those skilled in the art such as elution of silica gel flash column; preparative flash column purifications were also effected in some cases by use of disposal pre-packed multigram silica gel columns (RediSep) eluted with a CombiFlash system. Biotage™ and ISCO™ are also flash column instruments that may have been used in this invention for purification of intermediates.

For the purpose of judging compound identity and purity, LC/MS (liquid chromatography/mass spectroscopy) spectra were recorded using the following system. For measurement of mass spectra, the system consists of a Micromass Platform II spectrometer: ES Ionization in positive mode (mass range: 150-1200). The simultaneous chromatographic separation was achieved with the following HPLC system: ES Industries Chromegabond WR C-18 3u 120 Å (3.2×30 mm) column cartridge; Mobile Phase A: Water (0.02% TFA) and Phase B: Acetonitrile (0.02% TFA); gradient 10% B to 90% B in 3 minutes; equilibration time of 1 minute; flow rate of 2 mL/minute.

Many compounds of Formula 1 were also purified by reversed phased HPLC, using methods well known to those skilled in the art. In some cases, preparative HPLC purification was conducted using PE Sciex 150 EX Mass Spec controlling a Gilson 215 collector attached to a Shimadzu preparative HPLC system and a Leap autoinjector. Compounds were collected from the elution stream using LC/MS detection in the positive ion detection: The elution of compounds from C-18 columns (2.0×10 cm eluting at 20 mL/min) was effected using appropriate linear gradation mode over 10 minutes of Solvent (A) 0.05% TFA/H$_2$O and Solvent (B) 0.035% TFA/acetonitrile. For injection on to HPLC systems, the crude samples were dissolved in mixtures of methanol, acetonitrile and DMSO.

$^1$H-NMR characterization was performed using Bruker or Varian 300 or 400 MHz NMR Spectrometers.

The compounds of the present invention may be synthesized according to known techniques. The following examples and references are provided to aid the understanding of the present invention. The examples are not intended, however, to limit the invention, the true scope of which is set forth in the appended claims. The names of the final products in the examples were generated using Isis AutoNom 2000.

Preparation of Intermediates

Intermediate 1

[4-(2,3-Difluoro-phenoxy)-2-methyl-phenyl]-hydrazine

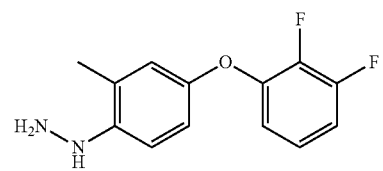 [SMILES: Cc1cc(Oc2cccc(F)c2F)ccc1NN]

Step 1:
4-(2,3-Difluoro-phenoxy)-2-methyl-1-nitro-benzene

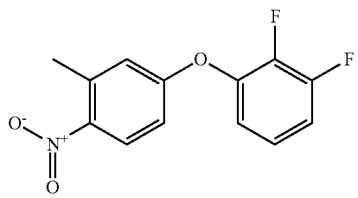 [SMILES: Cc1cc(Oc2cccc(F)c2F)ccc1[N+](=O)[O-]]

A mixture of 4-chloro-2-methyl-1-nitro-benzene (5 g, 29.1 mmol), 2,3-difluorophenol (4.55 g, 35.0 mmol) and $Cs_2CO_3$ (14.2 g, 43.7 mmol) in DMF (10 mL) was heated in a sealed tube in a microwave oven at 150° C. for 30 min. EtOAc (300 mL) was added and the mixture was washed with water (150 mL) and brine. The organic layer was dried ($Na_2SO_4$), filtered, and evaporated. The crude material was purified by flash chromatography (silica gel, 10% ethyl acetate in hexanes) to give 4-(2,3-difluoro-phenoxy)-2-methyl-1-nitro-benzene (5.6 g, 72%) as a light yellow oil.

Step 2:
4-(2,3-Difluoro-phenoxy)-2-methyl-phenylamine

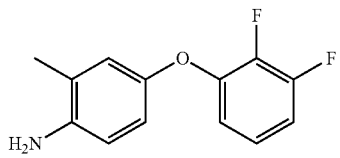 [SMILES: Cc1cc(Oc2cccc(F)c2F)ccc1N]

A mixture of 4-(2,3-difluoro-phenoxy)-2-methyl-1-nitro-benzene (5.28 g, 19.9 mmol) and palladium-on-carbon (587 mg) in MeOH (55 mL) was shaken under 30 psi of hydrogen in a Parr shaker for 4 h. The mixture was filtered through Celite and the Celite was washed with MeOH. The filtrate was evaporated to give 4-(2,3-difluoro-phenoxy)-2-methyl-phenylamine (4.56 g, 97%) which was used in the next step without further purification.

Step 3: [4-(2,3-Difluoro-phenoxy)-2-methyl-phenyl]-hydrazine

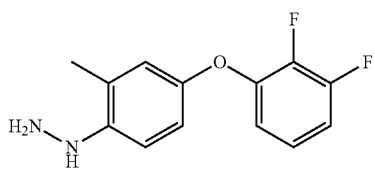 [SMILES: Cc1cc(Oc2cccc(F)c2F)ccc1NN]

A mixture of 4-(2,3-difluoro-phenoxy)-2-methyl-phenylamine (546 mg, 2.32 mmol) and conc. HCl (0.6 mL) in MeOH (1 mL) and water (2 mL) was cooled in an ice bath. A solution of $NaNO_2$ (168 mg, 2.44 mmol) in water (0.4 mL) was added slowly and the mixture was stirred for 30 min. The reaction mixture was transferred by pipette to a stirred solution of tin(II) chloride dihydrate (2.25 g, 10 mmol) in conc. HCl (5 mL) and the mixture was stirred for 4 h. MeOH (4 mL) was added, followed by 10 M NaOH until the pH reached 7-8. The solvent was evaporated under reduced pressure and the residue was dried under vacuum for 1 h. The residue was triturated with 10% $MeOH/CH_2Cl_2$, and the solid was filtered off and washed with 10% $MeOH/CH_2Cl_2$. The filtrate was evaporated under reduced pressure to give [4-(2,3-difluoro-phenoxy)-2-methyl-phenyl]-hydrazine (495 mg, 68%) as a yellow oil. This material was used in the next step without further purification.

Intermediate 2

3-(4-Hydrazino-3-methyl-phenoxy)-benzonitrile

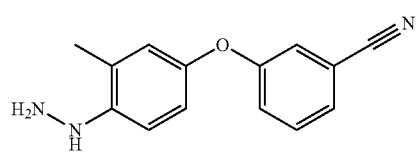 [SMILES: Cc1cc(Oc2cccc(C#N)c2)ccc1NN]

A mixture of 3-(4-amino-3-methyl-phenoxy)-benzonitrile (which may be prepared as described in Akama, T. et al. *Bioorg. Med. Chem. Lett.* 2009, 19, 2129-2132; 2.2 g, 9.8 mmol) and conc. HCl (3.5 mL) in MeOH (7 mL) and water (5 mL) was cooled in an ice bath. A solution of $NaNO_2$ (1.35 g, 19.6 mmol) in water (6 mL) was added slowly and the mixture was stirred for 30 min. The reaction mixture was transferred by pipette to a stirred solution of tin(II) chloride dihydrate (8.85 g, 39.2 mmol) in conc. HCl (7 mL) and the mixture was stirred for 30 min. MeOH (10 mL) was added, followed by 10 M NaOH until the pH reached 7-8. Water (100 mL) was added and the mixture was extracted with EtOAc (500 mL). The organic layer was washed with brine ($Na_2SO_4$), filtered, and evaporated to give 3-(4-hydrazino-3-methyl-phenoxy)-benzonitrile (2.2 g, 94%) as an oil. This material was used in the next step without further purification.

Example I-1

{5-Amino-1-[4-(2,3-difluoro-phenoxy)-2-methyl-phenyl]-1H-pyrazol-4-yl}-(4-bromo-1H-indol-2-yl)-methanone

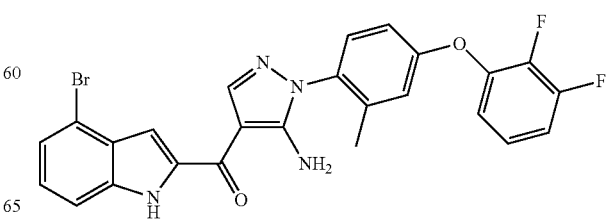

Step 1: 1-Benzenesulfonyl-4-bromo-1H-indole-2-carboxylic acid methyl ester

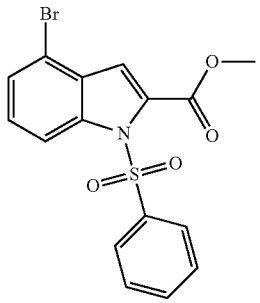 [SMILES: COC(=O)c1cc2c(Br)cccc2n1S(=O)(=O)c1ccccc1]

DIPEA (2.6 mL, 14.8 mmol) and MeOH (3 mL, 74.2 mmol) were added to a solution of 1-benzenesulfonyl-4-bromo-1H-indole-2-carbonyl chloride (which may be prepared as described in Mahboobi, S. et al. *J. Med. Chem.* 2006, 49, 3101-3115; 1.97 g, 4.94 mmol). The mixture was stirred at room temperature overnight, and the solvent was evaporated under reduced pressure. The residue was triturated with 15% EtOAc/hexanes, filtered, washed with 15% EtOAc/hexanes, and dried under vacuum overnight to give 1-benzenesulfonyl-4-bromo-1H-indole-2-carboxylic acid methyl ester (1.78 g, 91%).

Step 2: 3-(1-Benzenesulfonyl-4-bromo-1H-indol-2-yl)-3-oxo-propionitrile

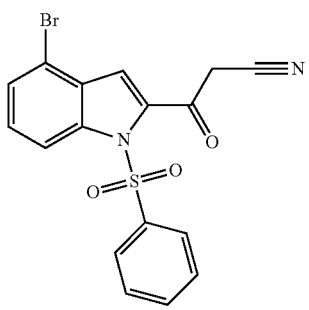 [SMILES: N#CCC(=O)c1cc2c(Br)cccc2n1S(=O)(=O)c1ccccc1]

A solution of methyl 4-bromo-1-(phenylsulfonyl)-1H-indole-2-carboxylate (970 mg, 2.46 mmol) and acetonitrile (770 μL, 14.8 mmol) in THF (25 mL) was cooled to −78° C. LDA (2M/THF) (2.5 ml, 5 mmol) was added slowly over 5 min. The reaction mixture was stirred at −78° C. for 30 min and then saturated NH$_4$Cl solution (40 mL) was added. Water (150 mL) was added and the mixture was extracted with EtOAc (500 mL). The organic layer was washed with brine, dried (Na$_2$SO$_4$), filtered, and evaporated. The residue was purified by chromatography (silica gel, 30% EtOAc/hexanes) to give 3-(4-bromo-1-(phenylsulfonyl)-1H-indol-2-yl)-3-oxopropanenitrile (650 mg, 66%) as a foam.

Step 3: (E)-2-(1-Benzenesulfonyl-4-bromo-1H-indole-2-carbonyl)-3-dimethylamino-acrylonitrile

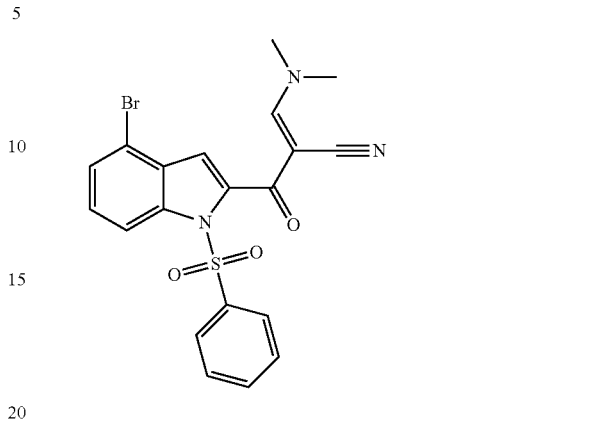

N,N-dimethylformamide dimethyl acetal (465 mg, 3.9 mmol) was added to a solution of 3-(4-bromo-1-(phenylsulfonyl)-1H-indol-2-yl)-3-oxopropanenitrile (1.21 g, 3.00 mmol) in toluene (20 mL), and the mixture was stirred at room temperature overnight. The solvent was removed under reduced pressure. The residue was purified by chromatography (silica gel, 70% EtOAc/hexanes) to give (E)-2-(1-benzenesulfonyl-4-bromo-1H-indole-2-carbonyl)-3-dimethylamino-acrylonitrile (1.06 g, 77%) as a yellow foam.

Step 4: {5-Amino-1-[4-(2,3-difluoro-phenoxy)-2-methyl-phenyl]-1H-pyrazol-4-yl}-(1-benzenesulfonyl-4-bromo-1H-indol-2-yl)-methanone

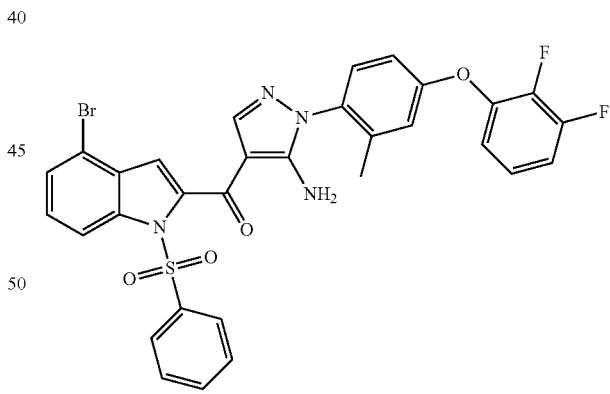

A mixture of [4-(2,3-difluoro-phenoxy)-2-methyl-phenyl]-hydrazine (which may be prepared as described for Intermediate 1; 816 mg, 3.26 mmol), (E)-2-(1-benzenesulfonyl-4-bromo-1H-indole-2-carbonyl)-3-dimethylamino-acrylonitrile (650 mg, 1.42 mmol) and EtOH (25 mL) was heated at reflux overnight. The solvent was removed under reduced pressure. The residue was purified by chromatography (silica gel, 30% EtOAc/hexanes) to give {5-amino-1-[4-(2,3-difluoro-phenoxy)-2-methyl-phenyl]-1H-pyrazol-4-yl}-(1-benzenesulfonyl-4-bromo-1H-indol-2-yl)-methanone (820 mg, 87%) as a foam.

Step 5: {5-Amino-1-[4-(2,3-difluoro-phenoxy)-2-methyl-phenyl]-1H-pyrazol-4-yl}-(4-bromo-1H-indol-2-yl)-methanone

A mixture of {5-amino-1-[4-(2,3-difluoro-phenoxy)-2-methyl-phenyl]-1H-pyrazol-4-yl}-(1-benzenesulfonyl-4-bromo-1H-indol-2-yl)-methanone (275 mg, 0.414 mmol), Cs₂CO₃ (540 mg, 1.66 mmol), THF (10 mL) and MeOH (5 mL) was stirred at room temperature overnight. The solvent was removed under reduced pressure. The residue was purified by chromatography (silica gel, 40% EtOAc/hexanes) to give {5-amino-1-[4-(2,3-difluoro-phenoxy)-2-methyl-phenyl]-1H-pyrazol-4-yl}-(4-bromo-1H-indol-2-yl)-methanone (210 mg, 97%) as an off-white solid. ¹H NMR (400 MHz, DMSO-d₆) δ ppm 12.10 (s, 1 H), 8.28 (s, 1 H), 7.51 (d, J=8.3 Hz, 1 H), 7.25-7.42 (m, 4 H), 7.15-7.23 (m, 3 H), 7.09 (t, J=7.5 Hz, 1 H), 7.03 (d, J=8.5 Hz, 1 H), 6.96 (br. s., 2 H), 2.09 (s, 3 H). MS calcd. for $C_{25}H_{18}BrF_2N_4O_2$ [(M+H)⁺] 523, obsd. 522.9.

Example I-2

{5-Amino-1-[4-(2,3-difluoro-phenoxy)-2-methyl-phenyl]-1H-pyrazol-4-yl}-(4-phenyl-1H-indol-2-yl)-methanone

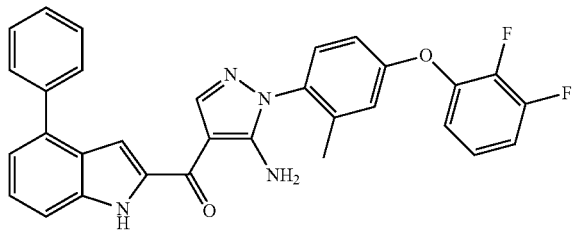

Step 1: {5-Amino-1-[4-(2,3-difluoro-phenoxy)-2-methyl-phenyl]-1H-pyrazol-4-yl}-(1-benzenesulfonyl-4-phenyl-1H-indol-2-yl)-methanone

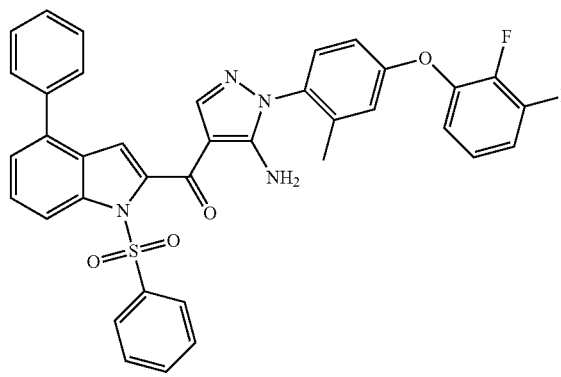

A mixture of {5-amino-1-[4-(2,3-difluoro-phenoxy)-2-methyl-phenyl]-1H-pyrazol-4-yl}-(1-benzenesulfonyl-4-bromo-1H-indol-2-yl)-methanone (which may be prepared as described in Example I-1 Step 4; 30 mg, 0.045 mmol), phenylboronic acid (11 mg, 0.09 mmol), Pd(PPh₃)₄ (5.2 mg, 0.004 mmol), K₂CO₃ (25 mg, 0.18 mmol), water (0.5 mL), toluene (1 mL), and EtOH (1 mL) was heated at 90° C. overnight. Water (2 mL) was added, and the mixture was extracted with EtOAc (2×5 mL). The organic layer was evaporated. The residue was purified by chromatography (silica gel, 30% EtOAc/hexanes) to give {5-amino-1-[4-(2,3-difluoro-phenoxy)-2-methyl-phenyl]-1H-pyrazol-4-yl}-(1-benzenesulfonyl-4-phenyl-1H-indol-2-yl)-methanone (28 mg, 94%) as an oil.

Step 2: {5-Amino-1-[4-(2,3-difluoro-phenoxy)-2-methyl-phenyl]-1H-pyrazol-4-yl}-(4-phenyl-1H-indol-2-yl)-methanone

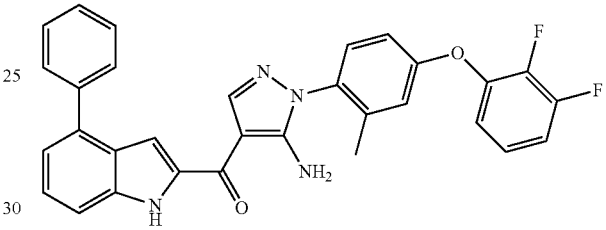

A mixture of {5-amino-1-[4-(2,3-difluoro-phenoxy)-2-methyl-phenyl]-1H-pyrazol-4-yl}-(1-benzenesulfonyl-4-phenyl-1H-indol-2-yl)-methanone (28 mg, 0.04 mmol), Cs₂CO₃ (41.4 mg, 0.13 mmol), THF (2 mL) and MeOH (1 mL) was stirred at room temperature overnight. The solvent was removed under reduced pressure. The residue was purified by chromatography (silica gel, 40% EtOAc/hexanes) to give {5-amino-1-[4-(2,3-difluoro-phenoxy)-2-methyl-phenyl]-1H-pyrazol-4-yl}-(4-phenyl-1H-indol-2-yl)-methanone (20 mg, 86%) as a light yellow oil. ¹H NMR (400 MHz, CDCl₃) δ ppm 9.65 (s, 1 H), 8.17 (s, 1 H), 7.72 (dd, J=8.4, 1.4 Hz, 2 H), 7.48-7.56 (m, 3 H), 7.37-7.46 (m, 3 H), 7.31 (d, J=8.6 Hz, 1 H), 7.26 (s, 1 H), 7.23 (dd, J=6.8, 1.4 Hz, 1 H), 7.07 (d, J=5.5 Hz, 2 H), 6.99 (d, J=2.7 Hz, 1 H), 6.92 (dt, J=8.1, 2.6 Hz, 2 H), 2.17 (s, 3 H). MS calcd. for $C_{31}H_{23}F_2N_4O_2$ [(M+H)⁺] 521, obsd. 521.1.

Example I-3

{5-Amino-1-[4-(2,3-difluoro-phenoxy)-2-methyl-phenyl]-1H-pyrazol-4-yl}-(4-thiophen-3-yl-1H-indol-2-yl)-methanone

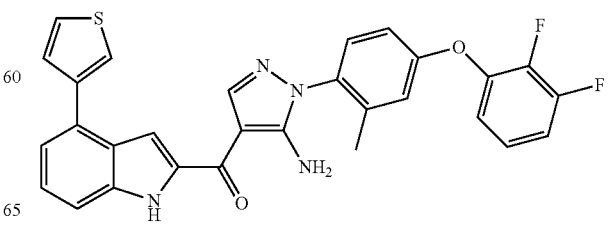

Step 1: {5-Amino-1-[4-(2,3-difluoro-phenoxy)-2-methyl-phenyl]-1H-pyrazol-4-yl}-(1-benzenesulfo-nyl-4-thiophen-3-yl-1H-indol-2-yl)-methanone

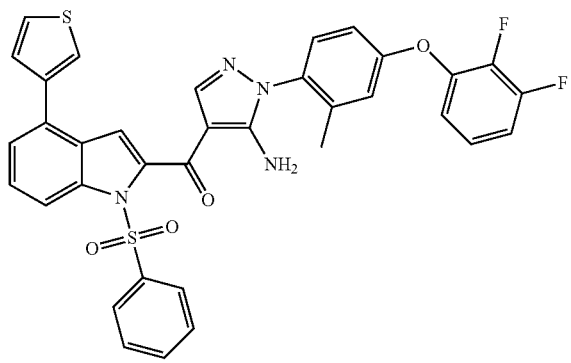 [SMILES: Cc1cc(Oc2cccc(F)c2F)ccc1-n1ncc(C(=O)c2cc3c(-c4ccsc4)cccc3n2S(=O)(=O)c2ccccc2)c1N]

A mixture of {5-amino-1-[4-(2,3-difluoro-phenoxy)-2-methyl-phenyl]-1H-pyrazol-4-yl}-(1-benzenesulfonyl-4-bromo-1H-indol-2-yl)-methanone (which may be prepared as described in Example I-1 Step 4; 95 mg, 0.14 mmol), thiophene-3-boronic acid (37 mg, 0.29 mmol), Pd(PPh₃)₄ (16.5 mg, 0.014 mmol), K₂CO₃ (79.2 mg, 0.57 mmol), water (1.5 mL), toluene (3 mL), and EtOH (3 mL) was heated at 90° C. overnight. Water (2 mL) was added, and the mixture was extracted with EtOAc (2×5 mL). The organic layer was evaporated. The residue was purified by chromatography (silica gel, 40% EtOAc/hexanes) to give {5-amino-1-[4-(2,3-difluoro-phenoxy)-2-methyl-phenyl]-1H-pyrazol-4-yl}-(1-benzenesulfonyl-4-thiophen-3-yl-1H-indol-2-yl)-methanone (94 mg, 92%) as an oil.

Step 2: {5-Amino-1-[4-(2,3-difluoro-phenoxy)-2-methyl-phenyl]-1H-pyrazol-4-yl}-(4-thiophen-3-yl-1H-indol-2-yl)-methanone

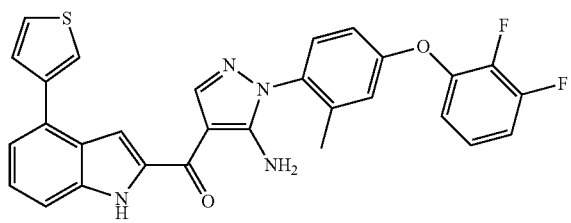 [SMILES: Cc1cc(Oc2cccc(F)c2F)ccc1-n1ncc(C(=O)c2cc3c(-c4ccsc4)cccc3[nH]2)c1N]

A mixture of {5-amino-1-[4-(2,3-difluoro-phenoxy)-2-methyl-phenyl]-1H-pyrazol-4-yl}-(1-benzenesulfonyl-4-thiophen-3-yl-1H-indol-2-yl)-methanone (94 mg, 0.14 mmol), Cs₂CO₃ (137 mg, 0.42 mmol), THF (6 mL) and MeOH (3 mL) was stirred at room temperature overnight. The solvent was removed under reduced pressure. The residue was purified by chromatography (silica gel, 40% EtOAc/hexanes) to give {5-amino-1-[4-(2,3-difluoro-phenoxy)-2-methyl-phenyl]-1H-pyrazol-4-yl}-(4-thiophen-3-yl-1H-indol-2-yl)-methanone (70 mg, 88%) as an off-white solid. $^1$H NMR (400 MHz, CDCl₃) δ ppm 9.40 (s, 1 H), 8.20 (s, 1 H), 7.59-7.61 (m, 1 H), 7.54 (dd, J=2.3, 0.8 Hz, 1 H), 7.48-7.53 (m, 2 H), 7.40-7.44 (m, 1 H), 7.35-7.40 (m, 1 H), 7.27-7.34 (m, 2 H), 7.03-7.13 (m, 2 H), 7.00 (d, J=2.7 Hz, 1 H), 6.89-6.96 (m, 2 H), 2.17 (s, 3 H). MS calcd. for $C_{29}H_{21}F_2N_4O_2S$ [(M+H)⁺] 527, obsd. 527.

Example I-4

{5-Amino-1-[4-(2,3-difluoro-phenoxy)-2-methyl-phenyl]-1H-pyrazol-4-yl}-(4-pyrazol-1-yl-1H-indol-2-yl)-methanone

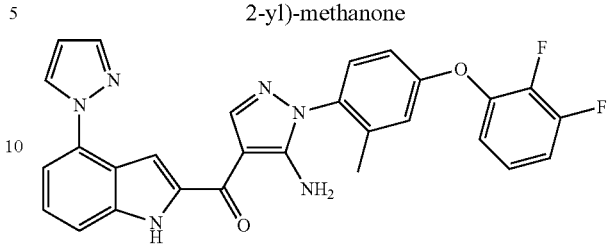

A mixture of {5-amino-1-[4-(2,3-difluoro-phenoxy)-2-methyl-phenyl]-1H-pyrazol-4-yl}-(4-bromo-1H-indol-2-yl)-methanone (which may be prepared as described in Example I-1 Step 5; 100 mg, 0.15 mmol), pyrazole (20.5 mg, 0.3 mmol), L-proline (7 mg, 0.06 mmol), copper(I) iodide (6 mg, 0.03 mmol), and K₂CO₃ (62.5 mg, 0.45 mmol) in DMSO (2 mL) was flushed with argon. The mixture was heated at 130° C. for 40 h and then purified by preparative HPLC to give {5-amino-1-[4-(2,3-difluoro-phenoxy)-2-methyl-phenyl]-1H-pyrazol-4-yl}-(4-pyrazol-1-yl-1H-indol-2-yl)-methanone (6 mg, 8%) as a yellow powder. $^1$H NMR (400 MHz, CDCl₃) δ ppm 9.44 (br. s., 1 H), 8.29 (s, 1 H), 8.08 (dd, J=2.5, 0.5 Hz, 1 H), 7.83-7.93 (m, 2 H), 7.71 (s, 1 H), 7.39-7.48 (m, 2 H), 7.31-7.37 (m, 2 H), 7.05-7.17 (m, 2 H), 7.03 (d, J=2.8 Hz, 1 H), 6.91-7.00 (m, 2 H), 6.57-6.59 (m, 1 H), 2.20 (s, 3 H). MS calcd. for $C_{28}H_{21}F_2N_6O_2$ [(M+H)⁺] 511, obsd. 511.

Example I-5

{5-Amino-1-[4-(2,3-difluoro-phenoxy)-2-methyl-phenyl]-1H-pyrazol-4-yl}-(4-thiophen-2-yl-1H-indol-2-yl)-methanone

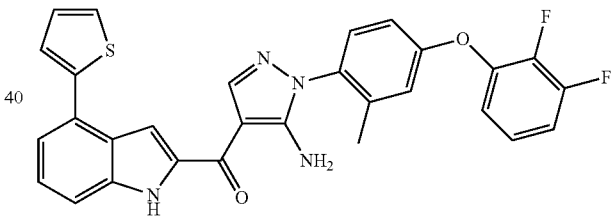

Step 1: {5-Amino-1-[4-(2,3-difluoro-phenoxy)-2-methyl-phenyl]-1H-pyrazol-4-yl}-(1-benzenesulfo-nyl-4-thiophen-2-yl-1H-indol-2-yl)-methanone

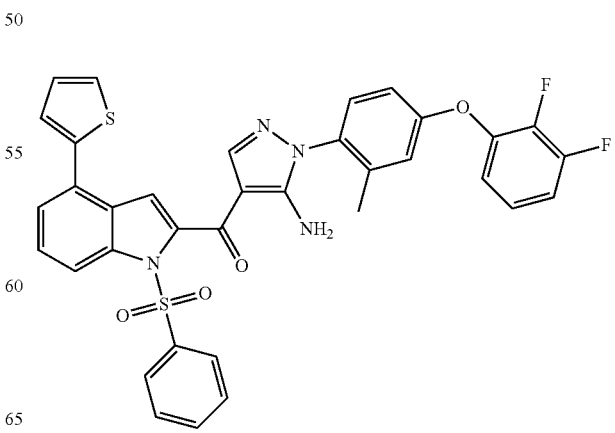

A mixture of {5-amino-1-[4-(2,3-difluoro-phenoxy)-2-methyl-phenyl]-1H-pyrazol-4-yl}-(1-benzenesulfonyl-4-bromo-1H-indol-2-yl)-methanone (which may be prepared as described in Example I-1 Step 4; 60 mg, 0.09 mmol), 2-(tributylstannyl)thiophene (67.5 mg, 0.18 mmol), Pd(PPh$_3$)$_4$ (10.4 mg, 0.009 mmol), and toluene (2 mL) was heated at 100° C. overnight. The solvent was evaporated. The residue was purified by chromatography (silica gel, 35% EtOAc/hexanes) to give {5-amino-1-[4-(2,3-difluoro-phenoxy)-2-methyl-phenyl]-1H-pyrazol-4-yl}-(1-benzenesulfonyl-4-thiophen-2-yl-1H-indol-2-yl)-methanone (46 mg, 76%) as an oil.

Step 2: {5-Amino-1-[4-(2,3-difluoro-phenoxy)-2-methyl-phenyl]-1H-pyrazol-4-yl}-(4-thiophen-2-yl-1H-indol-2-yl)-methanone

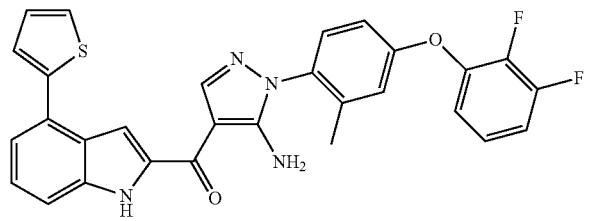 [SMILES: Cc1cc(Oc2cccc(F)c2F)ccc1-n1ncc(C(=O)c2cc3c(-c4cccs4)cccc3[nH]2)c1N]

A mixture of {5-amino-1-[4-(2,3-difluoro-phenoxy)-2-methyl-phenyl]-1H-pyrazol-4-yl}-(1-benzenesulfonyl-4-thiophen-2-yl-1H-indol-2-yl)-methanone (46 mg, 0.07 mmol), Cs$_2$CO$_3$ (67.4 mg, 0.21 mmol), THF (2 mL) and MeOH (1 mL) was stirred at room temperature overnight. The solvent was removed under reduced pressure. The residue was purified by chromatography (silica gel, 40% EtOAc/hexanes) to give {5-amino-1-[4-(2,3-difluoro-phenoxy)-2-methyl-phenyl]-1H-pyrazol-4-yl}-(4-thiophen-2-yl-1H-indol-2-yl)-methanone (32 mg, 88%) as an off-white solid. $^1$H NMR (400 MHz, CDCl$_3$) δ ppm 9.41 (br. s., 1 H), 8.24 (s, 1 H), 7.73 (dd, J=2.0, 0.8 Hz, 1 H), 7.49 (dd, J=3.5, 1.2 Hz, 1 H), 7.40-7.44 (m, 2 H), 7.36-7.39 (m, 2 H), 7.30-7.36 (m, 2 H), 7.20 (dd, J=5.1, 3.5 Hz, 1 H), 7.02-7.13 (m, 2 H), 7.00 (d, J=2.7 Hz, 1 H), 6.88-6.96 (m, 2 H), 2.18 (s, 3 H). MS calcd. for C$_{29}$H$_{21}$F$_2$N$_4$O$_2$S [(M+H)$^+$] 527, obsd. 526.9.

Example I-6

{5-Amino-1-[4-(2,3-difluoro-phenoxy)-2-methyl-phenyl]-1H-pyrazol-4-yl}-[4-(morpholine-4-carbonyl)-1H-indol-2-yl]-methanone trifluoroacetate salt

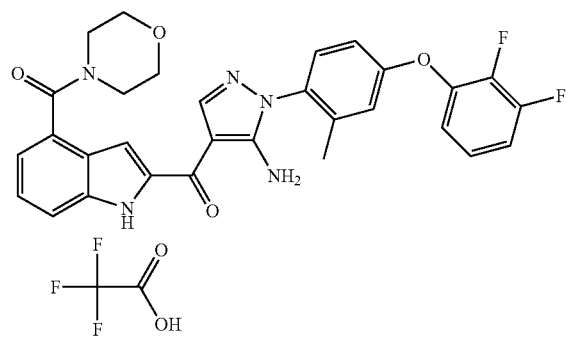

Carbon monoxide gas was bubbled through a mixture of {5-amino-1-[4-(2,3-difluoro-phenoxy)-2-methyl-phenyl]-1H-pyrazol-4-yl}-(4-bromo-1H-indol-2-yl)-methanone (which may be prepared as described in Example I-1 Step 5; 94 mg, 0.18 mmol), morpholine (313 mg, 3.6 mmol), Pd(PPh$_3$)$_4$ (62.3 mg, 0.054 mmol), and THF (10 mL) in a sealable tube for 5 min. The tube was sealed and heated at 90° C. for 2 h. The solvent was evaporated and the residue was purified by preparative HPLC to give {5-amino-1-[4-(2,3-difluoro-phenoxy)-2-methyl-phenyl]-1H-pyrazol-4-yl}-[4-(morpholine-4-carbonyl)-1H-indol-2-yl]-methanone trifluoroacetate salt (24 mg, 24%) as a light yellow powder. $^1$H NMR (400 MHz, CDCl$_3$) δ ppm 9.52 (s, 1 H), 8.23 (s, 1 H), 7.51 (d, J=8.2 Hz, 1 H), 7.30-7.38 (m, 3 H), 7.18 (dd, J=7.2, 1.0 Hz, 1 H), 7.02-7.15 (m, 2 H), 7.00 (d, J=2.7 Hz, 1 H), 6.88-6.96 (m, 2 H), 3.41-4.00 (m, 8 H), 2.17 (s, 3 H). MS calcd. for C$_{30}$H$_{26}$F$_2$N$_5$O$_4$ [(M+H)$^+$] 558, obsd. 558.

Example I-7

{5-Amino-1-[4-(2,3-difluoro-phenoxy)-2-methyl-phenyl]-1H-pyrazol-4-yl}-[4-(1-methyl-1H-pyrazol-3-yl)-1H-indol-2-yl]-methanone

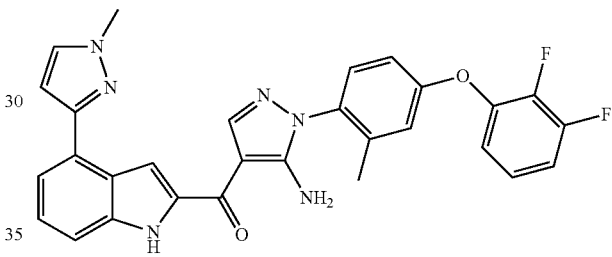

Step 1: {5-Amino-1-[4-(2,3-difluoro-phenoxy)-2-methyl-phenyl]-1H-pyrazol-4-yl}-[1-benzenesulfonyl-4-(1-methyl-1H-pyrazol-3-yl)-1H-indol-2-yl]-methanone

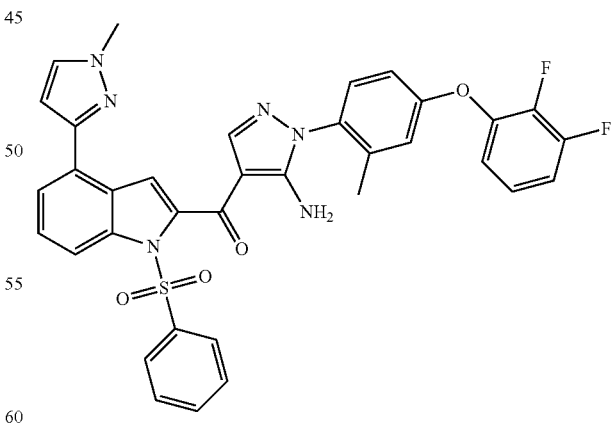

A mixture of {5-amino-1-[4-(2,3-difluoro-phenoxy)-2-methyl-phenyl]-1H-pyrazol-4-yl}-(1-benzenesulfonyl-4-bromo-1H-indol-2-yl)-methanone (which may be prepared as described in Example I-1 Step 4; 65 mg, 0.098 mmol), 1-methyl-1H-pyrazole-4-boronic acid hydrochloride (32 mg, 0.196 mmol), Pd(PPh$_3$)$_4$ (11.3 mg, 0.01 mmol), K$_2$CO$_3$ (54.2 mg, 0.39 mmol), water (1 mL), toluene (2 mL), and EtOH (2 mL) was heated at 90° C. overnight. Water (2 mL) was added, and the mixture was extracted with EtOAc (2×5 mL). The organic layer was evaporated. The residue was purified by chromatography (silica gel, 40% EtOAc/hexanes) to give {5-amino-1-[4-(2,3-difluoro-phenoxy)-2-methyl-phenyl]-1H-pyrazol-4-yl}-[1-benzenesulfonyl-4-(1-methyl-1H-pyrazol-3-yl)-1H-indol-2-yl]-methanone (31 mg, 48%) as an oil.

Step 2: {5-Amino-1-[4-(2,3-difluoro-phenoxy)-2-methyl-phenyl]-1H-pyrazol-4-yl}-[4-(1-methyl-1H-pyrazol-3-yl)-1H-indol-2-yl]-methanone

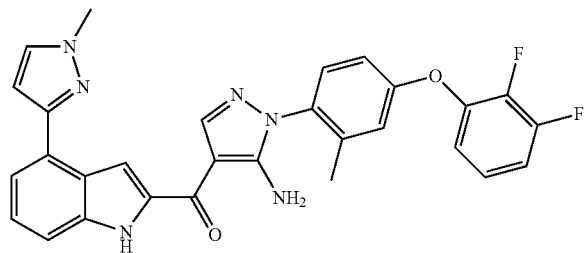 [SMILES: Cc1cc(Oc2cccc(F)c2F)ccc1-n1ncc(C(=O)c2cc3c(-c4ccn(C)n4)cccc3[nH]2)c1N]

A mixture of {5-amino-1-[4-(2,3-difluoro-phenoxy)-2-methyl-phenyl]-1H-pyrazol-4-yl}-[1-benzenesulfonyl-4-(1-methyl-1H-pyrazol-3-yl)-1H-indol-2-yl]-methanone (31 mg, 0.046 mmol), $Cs_2CO_3$ (60.8 mg, 0.19 mmol), THF (1.5 mL) and MeOH (0.75 mL) was stirred at room temperature overnight. The solvent was removed under reduced pressure. The residue was purified by chromatography (silica gel, 90% EtOAc/hexanes) to give {5-amino-1-[4-(2,3-difluoro-phenoxy)-2-methyl-phenyl]-1H-pyrazol-4-yl}-[4-(1-methyl-1H-pyrazol-3-yl)-1H-indol-2-yl]-methanone (21 mg, 86%) as an off-white solid. $^1$H NMR (400 MHz, $CDCl_3$) δ ppm 9.29 (s, 1 H), 8.21 (s, 1 H), 7.93 (s, 1 H), 7.78 (s, 1 H), 7.47-7.50 (m, 1 H), 7.30-7.37 (m, 3 H), 7.22 (dd, J=6.4, 1.8 Hz, 1 H), 7.02-7.14 (m, 2 H), 7.00 (d, J=2.7 Hz, 1 H), 6.86-6.96 (m, 2 H), 4.05 (s, 3 H), 2.18 (s, 3 H). MS calcd. for $C_{29}H_{23}F_2N_6O_2$ $[(M+H)^+]$ 525, obsd. 525.

Example I-8

{5-Amino-1-[4-(2,3-difluoro-phenoxy)-2-methyl-phenyl]-1H-pyrazol-4-yl}-(4-pyridin-2-yl-1H-indol-2-yl)-methanone

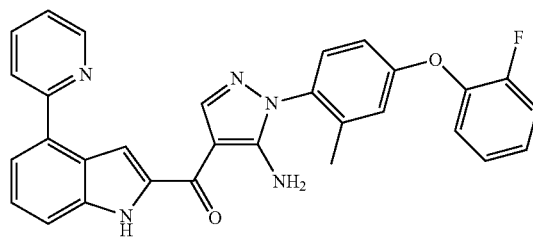

Step 1: {5-Amino-1-[4-(2,3-difluoro-phenoxy)-2-methyl-phenyl]-1H-pyrazol-4-yl}-(1-benzenesulfonyl-4-pyridin-2-yl-1H-indol-2-yl)-methanone

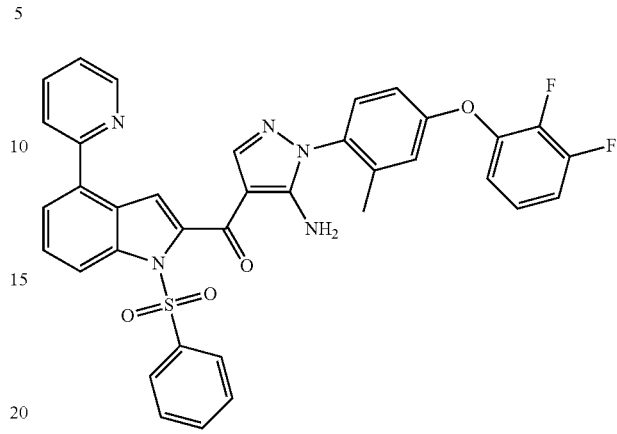

A mixture of {5-amino-1-[4-(2,3-difluoro-phenoxy)-2-methyl-phenyl]-1H-pyrazol-4-yl}-(1-benzenesulfonyl-4-bromo-1H-indol-2-yl)-methanone (which may be prepared as described in Example I-1 Step 4; 64 mg, 0.097 mmol), 2-(tributylstannyl)pyridine (71 mg, 0.19 mmol), $Pd(PPh_3)_4$ (11.1 mg, 0.01 mmol), and toluene (2 mL) was heated at 100° C. overnight. The solvent was evaporated. The residue was purified by chromatography (silica gel, 45% EtOAc/hexanes) to give {5-amino-1-[4-(2,3-difluoro-phenoxy)-2-methyl-phenyl]-1H-pyrazol-4-yl}-(1-benzenesulfonyl-4-pyridin-2-yl-1H-indol-2-yl)-methanone (27 mg, 42%) as an oil.

Step 2: {5-Amino-1-[4-(2,3-difluoro-phenoxy)-2-methyl-phenyl]-1H-pyrazol-4-yl}-(4-pyridin-2-yl-1H-indol-2-yl)-methanone

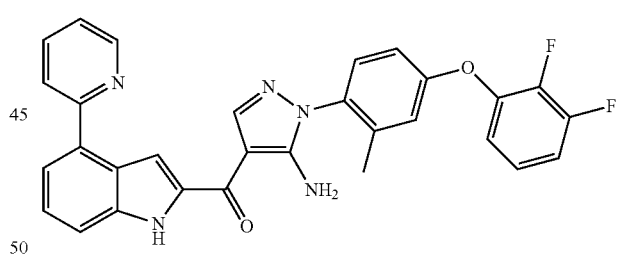

A mixture of {5-amino-1-[4-(2,3-difluoro-phenoxy)-2-methyl-phenyl]-1H-pyrazol-4-yl}-(1-benzenesulfonyl-4-pyridin-2-yl-1H-indol-2-yl)-methanone (27 mg, 0.041 mmol), $Cs_2CO_3$ (53.2 mg, 0.16 mmol), THF (2 mL) and MeOH (1 mL) was stirred at room temperature overnight. The solvent was removed under reduced pressure. The residue was purified by chromatography (silica gel, 50% EtOAc/hexanes) to give {5-amino-1-[4-(2,3-difluoro-phenoxy)-2-methyl-phenyl]-1H-pyrazol-4-yl}-(4-pyridin-2-yl-1H-indol-2-yl)-methanone (19 mg, 79%; purity 88%) as an off-white solid. $^1$H NMR (400 MHz, $CDCl_3$) δ ppm 9.37 (br. s., 1 H), 8.87 (d, J=4.8 Hz, 1 H), 8.29 (s, 1 H), 7.91 (d, J=18.1 Hz, 3 H), 7.44-7.65 (m, 3 H), 7.35 (d, J=8.5 Hz, 2 H), 7.04-7.18 (m, 2 H), 7.01-7.04 (m, 1 H), 6.88-6.99 (m, 2 H), 2.20 (s, 3 H). MS calcd. for $C_{30}H_{22}F_2N_5O_2$ $[(M+H)^+]$ 522, obsd. 522.

Example I-9

{5-Amino-1-[4-(2,3-difluoro-phenoxy)-2-methyl-phenyl]-1H-pyrazol-4-yl}-(4-benzyl-1H-indol-2-yl)-methanone

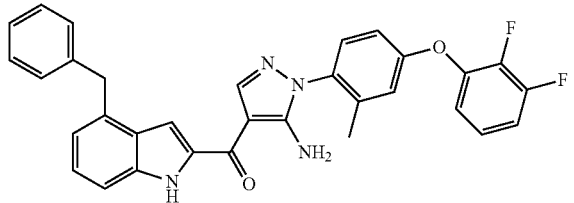 [SMILES: Cc1cc(Oc2cccc(F)c2F)ccc1-n1ncc(C(=O)c2cc3c(Cc4ccccc4)cccc3[nH]2)c1N]

Step 1: {5-Amino-1-[4-(2,3-difluoro-phenoxy)-2-methyl-phenyl]-1H-pyrazol-4-yl}-(1-benzenesulfonyl-4-benzyl-1H-indol-2-yl)-methanone

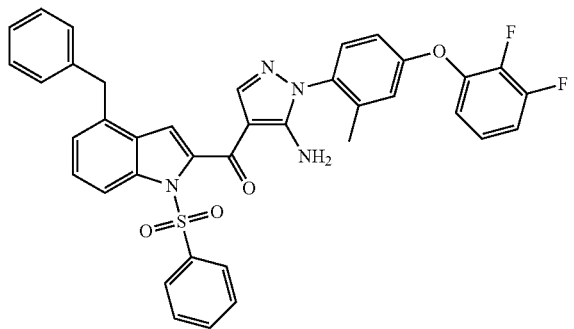 [SMILES: Cc1cc(Oc2cccc(F)c2F)ccc1-n1ncc(C(=O)c2cc3c(Cc4ccccc4)cccc3n2S(=O)(=O)c2ccccc2)c1N]

A mixture of {5-amino-1-[4-(2,3-difluoro-phenoxy)-2-methyl-phenyl]-1H-pyrazol-4-yl}-(1-benzenesulfonyl-4-bromo-1H-indol-2-yl)-methanone (which may be prepared as described in Example I-1 Step 4; 65 mg, 0.098 mmol), Pd(OAc)$_2$ (2.8 mg, 0.012 mmol), 2-dicyclohexylphosphino-2',6'-dimethoxybiphenyl (Aldrich; 9 mg, 0.022 mmol), and THF (2 mL) was flushed with argon for 3 min and then stirred at room temperature for 5 min. Benzylzinc(II) bromide (Aldrich; 0.5 M in THF; 0.3 mL; 0.15 mmol) was added and the mixture was heated at 75° C. for 2 h. The solvent was evaporated. The residue was purified by chromatography (silica gel, 35% EtOAc/hexanes) to give {5-amino-1-[4-(2,3-difluoro-phenoxy)-2-methyl-phenyl]-1H-pyrazol-4-yl}-(1-benzenesulfonyl-4-benzyl-1H-indol-2-yl)-methanone (66 mg, 82%) as an oil.

Step 2: {5-Amino-1-[4-(2,3-difluoro-phenoxy)-2-methyl-phenyl]-1H-pyrazol-4-yl}-(4-benzyl-1H-indol-2-yl)-methanone

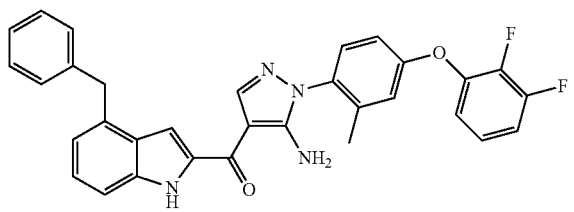 [SMILES: Cc1cc(Oc2cccc(F)c2F)ccc1-n1ncc(C(=O)c2cc3c(Cc4ccccc4)cccc3[nH]2)c1N]

A mixture of {5-amino-1-[4-(2,3-difluoro-phenoxy)-2-methyl-phenyl]-1H-pyrazol-4-yl}-(1-benzenesulfonyl-4-benzyl-1H-indol-2-yl)-methanone (63 mg, 0.093 mmol), Cs$_2$CO$_3$ (122 mg, 0.37 mmol), THF (5 mL) and MeOH (2.5 mL) was stirred at room temperature overnight. The solvent was removed under reduced pressure. The residue was purified by chromatography (silica gel, 40% EtOAc/hexanes) to give {5-amino-1-[4-(2,3-difluoro-phenoxy)-2-methyl-phenyl]-1H-pyrazol-4-yl}-(4-benzyl-1H-indol-2-yl)-methanone (42 mg, 84%) as a yellow oil. $^1$H NMR (400 MHz, CDCl$_3$) δ ppm 9.26 (br. s., 1 H), 8.06 (s, 1 H), 7.30-7.42 (m, 8 H), 7.25 (dd, J=2.1, 0.9 Hz, 2 H), 7.05-7.17 (m, 2 H), 6.91-7.04 (m, 4 H), 4.36 (s, 2 H), 2.19 (s, 3 H). MS calcd. for C$_{32}$H$_{25}$F$_2$N$_4$O$_2$ [(M+H)$^+$] 535, obsd. 536.

Example I-10

{5-Amino-1-[4-(2,3-difluoro-phenoxy)-2-methyl-phenyl]-1H-pyrazol-4-yl}-[4-(1H-pyrazol-4-yl)-1H-indol-2-yl]-methanone

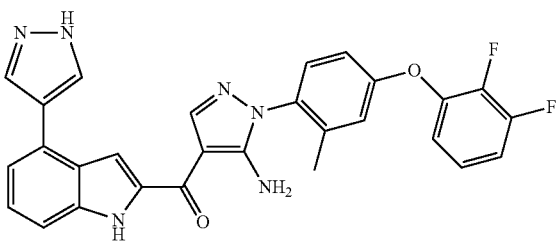 [SMILES: Cc1cc(Oc2cccc(F)c2F)ccc1-n1ncc(C(=O)c2cc3c(-c4cn[nH]c4)cccc3[nH]2)c1N]

A mixture of {5-amino-1-[4-(2,3-difluoro-phenoxy)-2-methyl-phenyl]-1H-pyrazol-4-yl}-(4-bromo-1H-indol-2-yl)-methanone (which may be prepared as described in Example I-1 Step 5; 55 mg, 0.105 mmol), tert-butoxycarbonyl-1H-pyrazole-4-boronic acid (44.6 mg, 0.21 mmol), Pd(PPh$_3$)$_4$ (12.1 mg, 0.011 mmol), K$_2$CO$_3$ (58.1 mg, 0.42 mmol), water (0.75 mL), toluene (1.5 mL), and EtOH (1.5 mL) was heated at 90° C. overnight. Water (2 mL) was added, and the mixture was extracted with EtOAc (2×5 mL). The organic layer was evaporated. The residue was purified by chromatography (silica gel, 60% EtOAc/hexanes) to give {5-amino-1-[4-(2,3-difluoro-phenoxy)-2-methyl-phenyl]-1H-pyrazol-4-yl}-[4-(1H-pyrazol-4-yl)-1H-indol-2-yl]-methanone (30 mg, 56%) as an oil. $^1$H NMR (400 MHz, DMSO-d$_6$) δ ppm 13.04 (br. s., 1 H), 11.78 (s, 1 H), 8.39-8.47 (m, 2 H), 8.07 (s, 1 H), 7.23-7.49 (m, 7 H), 7.17 (d, J=2.8 Hz, 1 H), 6.99-7.13 (m, 2 H), 6.90 (s, 2 H), 2.10 (s, 3 H). MS calcd. for C$_{28}$H$_{21}$F$_2$N$_6$O$_2$ [(M+H)$^+$] 511, obsd. 511.

Example I-11

3-(2-{5-Amino-1-[4-(2,3-difluoro-phenoxy)-2-methyl-phenyl]-1H-pyrazole-4-carbonyl}-1H-indol-4-yl)-benzonitrile

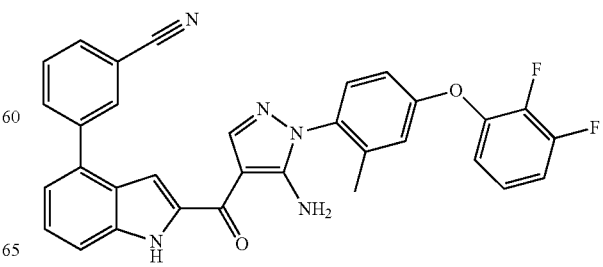

A mixture of {5-amino-1-[4-(2,3-difluoro-phenoxy)-2-methyl-phenyl]-1H-pyrazol-4-yl}-(4-bromo-1H-indol-2-yl)-methanone (which may be prepared as described in Example I-1 Step 5; 55 mg, 0.105 mmol), 3-cyanophenyl-boronic acid (30.9 mg, 0.21 mmol), Pd(PPh$_3$)$_4$ (12.1 mg, 0.011 mmol), K$_2$CO$_3$ (58.1 mg, 0.42 mmol), water (0.75 mL), toluene (1.5 mL), and EtOH (1.5 mL) was heated at 90° C. overnight. Water (2 mL) was added, and the mixture was extracted with EtOAc (2×5 mL). The organic layer was evaporated. The residue was purified by chromatography (silica gel, 35% EtOAc/hexanes) to give 3-(2-{5-amino-1-[4-(2,3-difluoro-phenoxy)-2-methyl-phenyl]-1H-pyrazole-4-carbonyl}-1H-indol-4-yl)-benzonitrile (38 mg, 66%) as an oil. $^1$H NMR (400 MHz, CDCl$_3$) δ ppm 9.43 (s, 1 H), 8.15 (s, 1 H), 7.96-8.01 (m, 2 H), 7.73-7.78 (m, 1 H), 7.64-7.70 (m, 1 H), 7.53-7.57 (m, 1 H), 7.42-7.49 (m, 1 H), 7.32-7.38 (m, 2 H), 7.23 (dd, J=7.2, 0.9 Hz, 1 H), 7.05-7.17 (m, 2 H), 7.02 (d, J=3.0 Hz, 1 H), 6.91-6.99 (m, 2 H), 2.20 (s, 3 H). MS calcd. for C$_{32}$H$_{22}$F$_2$N$_5$O$_2$ [(M+H)$^+$] 546, obsd. 546.

Example I-12

{5-Amino-1-[4-(2,3-difluoro-phenoxy)-2-methyl-phenyl]-1H-pyrazol-4-yl}-[4-(3-chloro-phenyl)-1H-indol-2-yl]-methanone

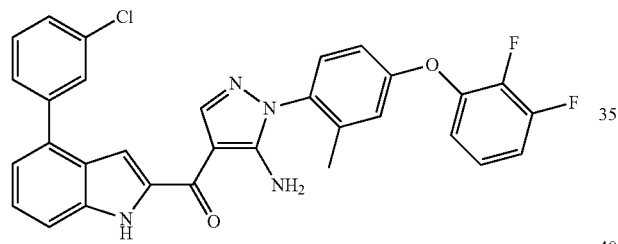

A mixture of {5-amino-1-[4-(2,3-difluoro-phenoxy)-2-methyl-phenyl]-1H-pyrazol-4-yl}-(4-bromo-1H-indol-2-yl)-methanone (which may be prepared as described in Example I-1 Step 5; 55 mg, 0.105 mmol), 3-chlorophenyl-boronic acid (32.9 mg, 0.21 mmol), Pd(PPh$_3$)$_4$ (12.1 mg, 0.011 mmol), K$_2$CO$_3$ (58.1 mg, 0.42 mmol), water (0.75 mL), toluene (1.5 mL), and EtOH (1.5 mL) was heated at 90° C. overnight. Water (2 mL) was added, and the mixture was extracted with EtOAc (2×5 mL). The organic layer was evaporated. The residue was purified by chromatography (silica gel, 35% EtOAc/hexanes) to give {5-amino-1-[4-(2,3-difluoro-phenoxy)-2-methyl-phenyl]-1H-pyrazol-4-yl}-[4-(3-chloro-phenyl)-1H-indol-2-yl]-methanone (54 mg, 87%) as an oil. $^1$H NMR (400 MHz, CDCl$_3$) δ ppm 9.41 (br. s., 1 H), 8.17 (s, 1 H), 7.71 (t, J=1.8 Hz, 1 H), 7.63 (dt, J=7.5, 1.4 Hz, 1 H), 7.48-7.53 (m, 2 H), 7.41-7.47 (m, 3 H), 7.34 (d, J=8.5 Hz, 1 H), 7.24 (dd, J=7.3, 1.0 Hz, 1 H), 7.05-7.16 (m, 2 H), 7.02 (d, J=2.5 Hz, 1 H), 6.90-6.99 (m, 2 H), 2.20 (s, 3 H). MS calcd. for C$_{31}$H$_{22}$Cl$_1$F$_2$N$_4$O$_2$ [(M+H)$^+$] 555, obsd. 555.

Example I-13

3-(2-{5-Amino-1-[4-(2,3-difluoro-phenoxy)-2-methyl-phenyl]-1H-pyrazole-4-carbonyl}-1H-indol-4-ylmethyl)-benzonitrile

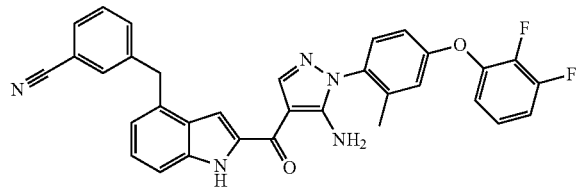 [SMILES: Cc1cc(Oc2cccc(F)c2F)ccc1-n1ncc(C(=O)c2cc3c(Cc4cccc(C#N)c4)cccc3[nH]2)c1N]

Step 1: 3-(2-{5-Amino-1-[4-(2,3-difluoro-phenoxy)-2-methyl-phenyl]-1H-pyrazole-4-carbonyl}-1-benzenesulfonyl-1H-indol-4-ylmethyl)-benzonitrile

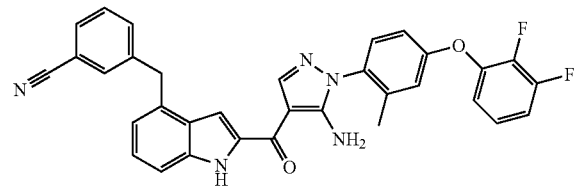 [SMILES: Cc1cc(Oc2cccc(F)c2F)ccc1-n1ncc(C(=O)c2cc3c(Cc4cccc(C#N)c4)cccc3[nH]2)c1N]

A mixture of {5-amino-1-[4-(2,3-difluoro-phenoxy)-2-methyl-phenyl]-1H-pyrazol-4-yl}-(1-benzenesulfonyl-4-bromo-1H-indol-2-yl)-methanone (which may be prepared as described in Example I-1 Step 4; 65 mg, 0.098 mmol), Pd(OAc)$_2$ (2.8 mg, 0.012 mmol), 2-dicyclohexylphosphino-2',6'-dimethoxybiphenyl (Aldrich; 9 mg, 0.022 mmol), and THF (2 mL) was flushed with argon for 3 min and then stirred at room temperature for 5 min. (3-Cyano-benzyl)zinc (II) bromide (Aldrich; 0.5 M in THF; 0.3 mL; 0.15 mmol) was added and the mixture was heated at 75° C. for 2 h. Water (3 mL) was added and the mixture was extracted with EtOAc (2×5 mL). The combined organic layers were evaporated. The residue was purified by chromatography (silica gel, 35% EtOAc/hexanes) to give 3-(2-{5-amino-1-[4-(2,3-difluoro-phenoxy)-2-methyl-phenyl]-1H-pyrazole-4-carbonyl}-1-benzenesulfonyl-1H-indol-4-ylmethyl)-benzonitrile (64 mg, 93%) as an oil.

Step 2: 3-(2-{5-Amino-1-[4-(2,3-difluoro-phenoxy)-2-methyl-phenyl]-1H-pyrazole-4-carbonyl}-1H-indol-4-ylmethyl)-benzonitrile A mixture of 3-(2-{5-amino-1-[4-(2,3-difluoro-phenoxy)-2-methyl-phenyl]-1H-pyrazole-4-carbonyl}-1-benzenesulfonyl-1H-indol-4-ylmethyl)-benzonitrile (64 mg, 0.092 mmol), Cs$_2$CO$_3$ (119 mg, 0.37 mmol), THF (5 mL) and MeOH (2.5 mL) was stirred at room temperature overnight. The solvent was removed under reduced pressure. The residue was purified by chromatography (silica gel, 40% EtOAc/hexanes) to give 3-(2-{5-amino-1-[4-(2,3-difluoro-phenoxy)-2-methyl-phenyl]-1H-pyrazole-4-carbonyl}-1H-indol-4-ylmethyl)-benzonitrile (40 mg, 78%) as a yellow oil. $^1$H NMR (400 MHz, CDCl$_3$) δ ppm 9.30 (br. s., 1 H), 8.07 (s, 1 H), 7.50-7.60 (m, 3 H), 7.43 (dd, J=11.2, 8.2 Hz, 2 H), 7.30-7.36 (m, 2 H), 7.20 (s, 1 H), 7.10 (ddd, J=15.2, 8.7, 5.9 Hz, 2 H), 7.02 (d, J=2.5 Hz, 1 H), 6.90-6.98 (m, 3 H), 4.39 (s, 2 H), 2.19 (s, 3 H). MS calcd. for C$_{33}$H$_{24}$F$_2$N$_5$O$_2$ [(M+H)$^+$] 560, obsd. 560.1.

Example I-14

3-(4-{5-Amino-4-[4-(1H-pyrazol-4-yl)-1H-indole-2-carbonyl]-pyrazol-1-yl}-3-methyl-phenoxy)-benzonitrile

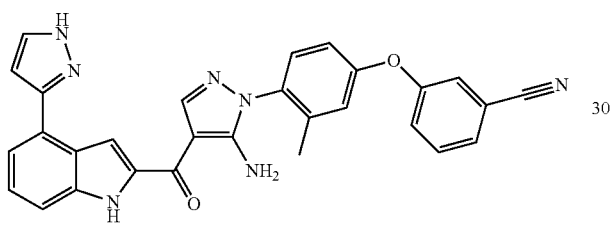

Step 1: 3-{4-[5-Amino-4-(1-benzenesulfonyl-4-bromo-1H-indole-2-carbonyl)-pyrazol-1-yl]-3-methyl-phenoxy}-benzonitrile

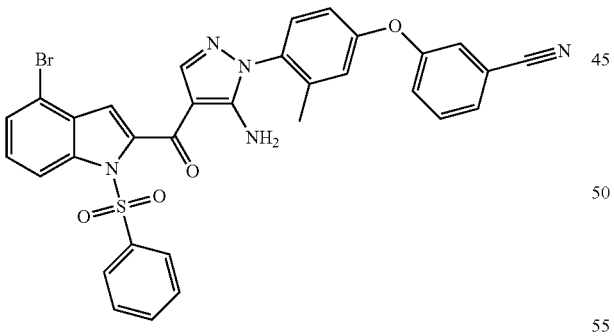

A mixture of 3-(4-hydrazino-3-methyl-phenoxy)-benzonitrile (which may be prepared as described for Intermediate 2; 789 mg, 3.3 mmol), (E)-2-(1-benzenesulfonyl-4-bromo-1H-indole-2-carbonyl)-3-dimethylamino-acrylonitrile (which may be prepared as described in Example I-1 Step 3; 510 mg, 1.11 mmol) and EtOH (30 mL) was heated at reflux overnight. The solvent was removed under reduced pressure. The residue was purified by chromatography (silica gel, 30% EtOAc/hexanes) to give 3-{4-[5-amino-4-(1-benzenesulfonyl-4-bromo-1H-indole-2-carbonyl)-pyrazol-1-yl]-3-methyl-phenoxy}-benzonitrile (598 mg, 82%) as a foam.

Step 2: 3-{4-[5-Amino-4-(4-bromo-1H-indole-2-carbonyl)-pyrazol-1-yl]-3-methyl-phenoxy}-benzonitrile

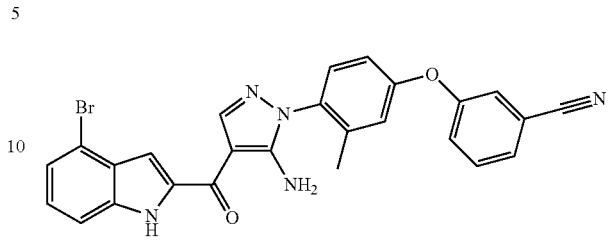

A mixture of 3-{4-[5-amino-4-(1-benzenesulfonyl-4-bromo-1H-indole-2-carbonyl)-pyrazol-1-yl]-3-methyl-phenoxy}-benzonitrile (450 mg, 0.69 mmol), Cs$_2$CO$_3$ (899 mg, 2.76 mmol), THF (15 mL) and MeOH (7.5 mL) was stirred at room temperature overnight. The solvent was removed under reduced pressure. The residue was purified by chromatography (silica gel, 40% EtOAc/hexanes) to give 3-{4-[5-amino-4-(4-bromo-1H-indole-2-carbonyl)-pyrazol-1-yl]-3-methyl-phenoxy}-benzonitrile.

Step 3: 3-(4-{5-Amino-4-[4-(1H-pyrazol-4-yl)-1H-indole-2-carbonyl]-pyrazol-1-yl}-3-methyl-phenoxy)-benzonitrile

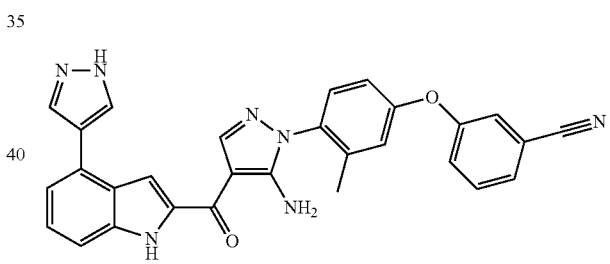

A mixture of 3-{4-[5-amino-4-(4-bromo-1H-indole-2-carbonyl)-pyrazol-1-yl]-3-methyl-phenoxy}-benzonitrile (55 mg, 0.107 mmol), 1-tert-butoxycarbonyl-1H-pyrazole-4-boronic acid (Combi-Blocks Inc., 7949 Silverton Avenue, Suite 915, San Diego, Calif. 92126, USA; 45.5 mg, 0.22 mmol), Pd(PPh$_3$)$_4$ (12.4 mg, 0.011 mmol), K$_2$CO$_3$ (59.3 mg, 0.43 mmol), water (0.75 mL), toluene (1.5 mL), and EtOH (1.5 mL) was heated at 90° C. overnight. Water (2 mL) was added, and the mixture was extracted with EtOAc (2×5 mL). The organic layer was evaporated. The residue was purified by chromatography (silica gel, 80% EtOAc/hexanes) to give 3-(4-{5-amino-4-[4-(1H-pyrazol-4-yl)-1H-indole-2-carbonyl]-pyrazol-1-yl}-3-methyl-phenoxy)-benzonitrile (30 mg, 56%) as an oil. $^1$H NMR (400 MHz, DMSO-d$_6$) δ ppm 13.04 (br. s., 1 H), 11.78 (s, 1 H), 8.38-8.49 (m, 2 H), 8.08 (br. s., 1 H), 7.56-7.71 (m, 3 H), 7.35-7.52 (m, 4 H), 7.19-7.30 (m, 3 H), 7.08 (dd, J=8.5, 2.8 Hz, 1 H), 6.92 (s, 2 H), 2.11 (s, 3 H). MS calcd. for C$_{29}$H$_{22}$N$_7$O$_2$ [(M+H)$^+$] 500, obsd. 500.

Example I-15

3-(4-{5-Amino-4-[4-(morpholine-4-carbonyl)-1H-indole-2-carbonyl]-pyrazol-1-yl}-3-methyl-phenoxy)-benzonitrile

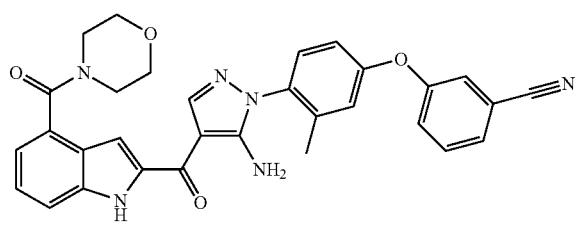 [SMILES: Cc1cc(Oc2cccc(C#N)c2)ccc1-n1ncc(C(=O)c2cc3c(C(=O)N4CCOCC4)cccc3[nH]2)c1N]

Carbon monoxide gas was bubbled through a mixture of 3-{4-[5-amino-4-(4-bromo-1H-indole-2-carbonyl)-pyrazol-1-yl]-3-methyl-phenoxy}-benzonitrile (which may be prepared as described in Example I-14 Step 2; 53 mg, 0.10 mmol), morpholine (180 mg, 2.1 mmol), Pd(PPh$_3$)$_4$ (35.9 mg, 0.031 mmol), and THF (10 mL) in a sealable tube for 5 min. The tube was sealed and heated at 90° C. overnight. The solvent was evaporated and the residue was purified by preparative HPLC to give 3-(4-{5-amino-4-[4-(morpholine-4-carbonyl)-1H-indole-2-carbonyl]-pyrazol-1-yl}-3-methyl-phenoxy)-benzonitrile (21 mg, 37%) as a light yellow powder. MS calcd. for $C_{31}H_{27}N_6O_4$ [(M+H)$^+$] 547, obsd. 546.9.

Example I-16

3-(4-{5-Amino-4-[4-(4-methyl-piperazine-1-carbonyl)-1H-indole-2-carbonyl]-pyrazol-1-yl}-3-methyl-phenoxy)-benzonitrile

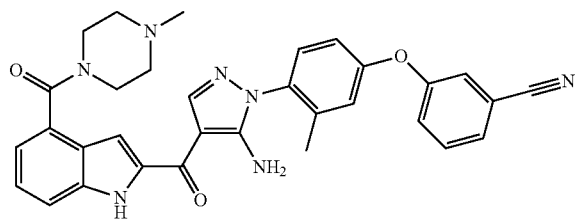 [SMILES: Cc1cc(Oc2cccc(C#N)c2)ccc1-n1ncc(C(=O)c2cc3c(C(=O)N4CCN(C)CC4)cccc3[nH]2)c1N]

Carbon monoxide gas was bubbled through a mixture of 3-{4-[5-amino-4-(4-bromo-1H-indole-2-carbonyl)-pyrazol-1-yl]-3-methyl-phenoxy}-benzonitrile (which may be prepared as described in Example I-14 Step 2; 53 mg, 0.10 mmol), 1-methylpiperazine (155 mg, 1.55 mmol), Pd(PPh$_3$)$_4$ (35.9 mg, 0.031 mmol), and THF (10 mL) in a sealable tube for 5 min. The tube was sealed and heated at 90° C. overnight. The solvent was evaporated and the residue was purified by preparative HPLC to give 3-(4-{5-amino-4-[4-(4-methyl-piperazine-1-carbonyl)-1H-indole-2-carbonyl]-pyrazol-1-yl}-3-methyl-phenoxy)-benzonitrile (32 mg, 55%) as an off-white foam. MS calcd. for $C_{32}H_{30}N_7O_3$ [(M+H)$^+$] 560, obsd. 560.

Example I-17

3-(4-{5-Amino-4-[4-(3-methoxy-benzyl)-1H-indole-2-carbonyl]-pyrazol-1-yl}-3-methyl-phenoxy)-benzonitrile

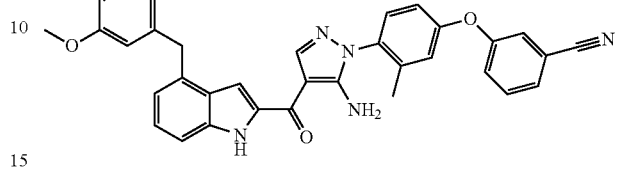

Step 1: 3-(4-{5-Amino-4-[1-benzenesulfonyl-4-(3-methoxy-benzyl)-1H-indole-2-carbonyl]-pyrazol-1-yl}-3-methyl-phenoxy)-benzonitrile

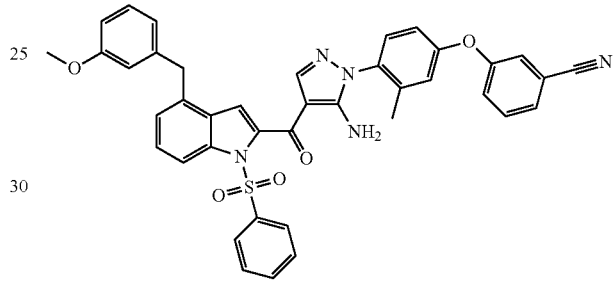

A mixture of 3-{4-[5-amino-4-(1-benzenesulfonyl-4-bromo-1H-indole-2-carbonyl)-pyrazol-1-yl]-3-methyl-phenoxy}-benzonitrile (which may be prepared as described in Example I-14 Step 1; 65 mg, 0.10 mmol), Pd(OAc)$_2$ (2.8 mg, 0.012 mmol), 2-dicyclohexylphosphino-2',6'-dimethoxybiphenyl (Aldrich; 9 mg, 0.022 mmol), and THF (2 mL) was flushed with argon for 5 min and then stirred at room temperature for 5 min. (3-Methoxy-benzyl)zinc(II) bromide (Aldrich; 0.5 M in THF; 0.3 mL; 0.15 mmol) was added and the mixture was heated at 75° C. for 2 h. Water (3 mL) was added and the mixture was extracted with EtOAc (2×5 mL). The combined organic layers were evaporated. The residue was purified by chromatography (silica gel, 40% EtOAc/hexanes) to give 3-(4-{5-amino-4-[1-benzenesulfonyl-4-(3-methoxy-benzyl)-1H-indole-2-carbonyl]pyrazol-1-yl}-3-methyl-phenoxy)-benzonitrile (62 mg, 90%) as an oil.

Step 2: 3-(4-{5-Amino-4-[4-(3-methoxy-benzyl)-1H-indole-2-carbonyl]-pyrazol-1-yl}-3-methyl-phenoxy)-benzonitrile

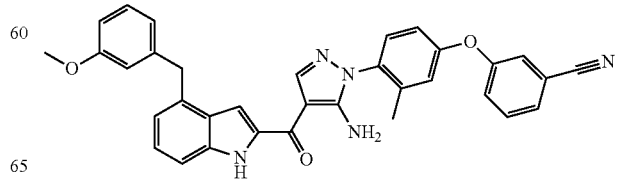

A mixture of 3-(4-{5-amino-4-[1-benzenesulfonyl-4-(3-methoxy-benzyl)-1H-indole-2-carbonyl]-pyrazol-1-yl}-3-methyl-phenoxy)-benzonitrile (62 mg, 0.089 mmol), Cs₂CO₃ (116 mg, 0.36 mmol), THF (5 mL) and MeOH (2.5 mL) was stirred at room temperature overnight. The solvent was removed under reduced pressure. The residue was purified by chromatography (silica gel, 40% EtOAc/hexanes) to give 3-(4-{5-amino-4-[4-(3-methoxy-benzyl)-1H-indole-2-carbonyl]pyrazol-1-yl}-3-methyl-phenoxy)-benzonitrile (41 mg, 83%) as a yellow foam. ¹H NMR (400 MHz, CDCl₃) δ ppm 9.28 (s, 1 H), 8.11 (s, 1 H), 7.44-7.56 (m, 2 H), 7.37-7.42 (m, 2 H), 7.30-7.37 (m, 4 H), 7.25 (d, J=8.0 Hz, 1 H), 6.91-7.08 (m, 5 H), 6.77-6.87 (m, 2 H), 4.34 (s, 2 H), 3.78 (s, 3 H), 2.22 (s, 3 H). MS calcd. for C₃₄H₂₈N₅O₃ [(M+H)⁺] 554, obsd. 554.1.

Example I-18

2-{5-Amino-1-[4-(2,3-difluoro-phenoxy)-2-methyl-phenyl]-1H-pyrazole-4-carbonyl}-1H-indole-4-carboxylic acid methyl ester

Carbon monoxide gas was bubbled through a mixture of {5-amino-1-[4-(2,3-difluoro-phenoxy)-2-methyl-phenyl]-1H-pyrazol-4-yl}-(4-bromo-1H-indol-2-yl)-methanone (which may be prepared as described in Example I-1 Step 5; 200 mg, 0.38 mmol), MeOH (2.5 mL, 62 mmol), Pd(PPh₃)₄ (132 mg, 0.115 mmol), and THF (20 mL) in a sealable tube for 5 min. The tube was sealed and heated at 90° C. overnight. The solvent was evaporated and the residue was purified by chromatography (silica gel, 45% EtOAc/hexanes) to give 2-{5-amino-1-[4-(2,3-difluoro-phenoxy)-2-methyl-phenyl]-1H-pyrazole-4-carbonyl}-1H-indole-4-carboxylic acid methyl ester (101 mg, 45%; 85% purity) as an oil. ¹H NMR (400 MHz, CDCl₃) δ ppm 9.52 (br. s., 1 H), 8.26 (s, 1 H), 7.87-7.95 (m, 2 H), 7.60 (d, J=8.3 Hz, 2 H), 7.43 (d, J=5.5 Hz, 2 H), 7.23-7.35 (m, 3 H), 7.19 (s, 2 H), 7.11 (d, J=7.5 Hz, 2 H), 6.96-7.05 (m, 3 H), 6.94 (d, J=2.8 Hz, 1 H), 6.79-6.90 (m, 2 H), 3.96 (s, 3 H), 2.11 (s, 3 H). MS calcd. for C₂₇H₂₁F₂N₄O₄ [(M+H)⁺] 503, obsd. 502.9.

Example I-19

{5-Amino-1-[4-(2,3-difluoro-phenoxy)-2-methyl-phenyl]-1H-pyrazol-4-yl}-(4-morpholin-4-ylmethyl-1H-indol-2-yl)-methanone

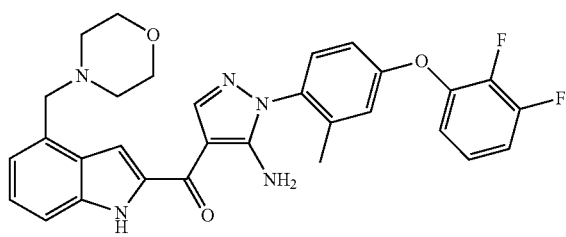 [SMILES: Cc1cc(Oc2cccc(F)c2F)ccc1-n1ncc(C(=O)c2cc3c(CN4CCOCC4)cccc3[nH]2)c1N]

Step 1: (1-Benzenesulfonyl-1H-indol-4-yl)-morpholin-4-yl-methanone

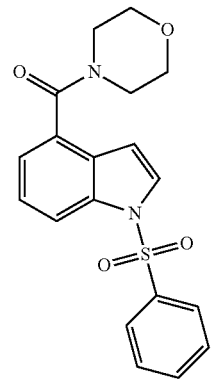 [SMILES: O=C(c1cccc2c1ccn2S(=O)(=O)c1ccccc1)N1CCOCC1]

A sealed tube containing 1-benzenesulfonyl-4-bromo-1H-indole (which may be prepared as described in Bell, I. M. et al. WO 2007061694 Page 103; 5.18 g, 59.5 mmol), Pd(PPh₃)₄ (1.37 g, 1.19 mmol), and THF (125 mL) was charged with 40 psi of carbon monoxide. The mixture was heated at 95° C. overnight and then the solvent was evaporated. The residue was purified by chromatography (silica gel, 80% EtOAc/hexanes) to give (1-benzenesulfonyl-1H-indol-4-yl)-morpholin-4-yl-methanone (2.67 g, 61%) as a foam.

Step 2: (1-Benzenesulfonyl-1H-indol-4-yl)-methanol

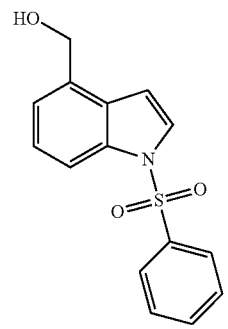 [SMILES: O=S(=O)(c1ccccc1)n1ccc2c(CO)cccc21]

A solution of (1-benzenesulfonyl-1H-indol-4-yl)-morpholin-4-yl-methanone (2.07 g, 5.59 mmol) in THF (50 mL) was cooled to −20° C. and LiAlH₄ (2 M in THF; 6.2 mL, 12.4 mmol) was added dropwise. The mixture was stirred for 30 min and MeOH (20 ML) was added. NaBH₄ (634 mg, 16.8 mmol) was added and the mixture was stirred for 30 min. EtOAc (300 mL) was added and the mixture was washed with brine. The organic layer was dried (Na₂SO₄), filtered, and evaporated to give (1-benzenesulfonyl-1H-indol-4-yl)-methanol (1.41 g, 88%) as an oil which was used directly in the next step without further purification.

Step 3: 1-Benzenesulfonyl-4-chloromethyl-1H-indole

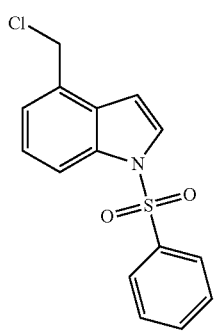 [SMILES: O=S(=O)(c1ccccc1)n1ccc2c(CCl)cccc21]

DIPEA (3.17 g, 24.5 mmol) and methanesulfonyl chloride (1.69 g, 14.7 mmol) were added to a solution of (1-benzenesulfonyl-1H-indol-4-yl)-methanol (1.41 g, 4.91 mmol) in THF (40 mL). The mixture was stirred at room temperature overnight. The solvent was evaporated under reduced pressure. The residue was purified by chromatography (silica gel, 20% EtOAc/hexanes) to give 1-benzenesulfonyl-4-chloromethyl-1H-indole (1.4 g, 93%) as an oil.

Step 4: 1-Benzenesulfonyl-4-morpholin-4-ylmethyl-1H-indole

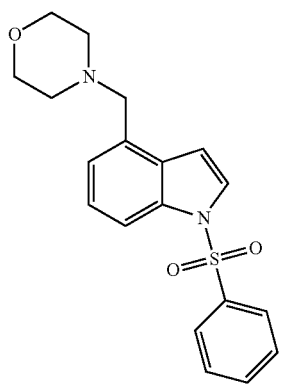 [SMILES: O=S(=O)(c1ccccc1)n1ccc2c(CN3CCOCC3)cccc21]

A mixture of 1-benzenesulfonyl-4-chloromethyl-1H-indole (1.4 g, 4.58 mmol), morpholine (1.2 mL, 13.7 mmol), $K_2CO_3$ (3.16 g, 22.9 mmol) and $CH_3CN$ (60 mL) was heated at 65° C. overnight. EtOAc (250 mL) was added and the mixture was washed with water and brine, dried ($Na_2SO_4$), filtered, and evaporated. The residue was purified by chromatography (silica gel, 60% EtOAc/hexanes) to give 1-benzenesulfonyl-4-morpholin-4-ylmethyl-1H-indole (1.45 g, 89%) as an oil.

Step 5: 1-Benzenesulfonyl-4-morpholin-4-ylmethyl-1H-indole-2-carboxylic acid

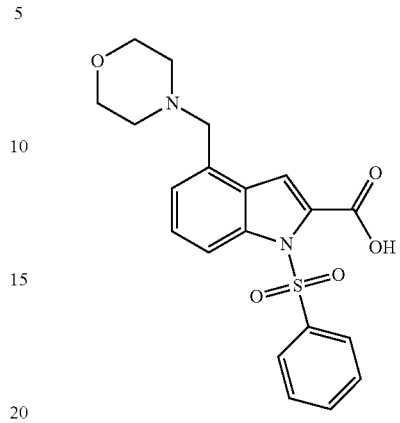

A solution of 1-benzenesulfonyl-4-morpholin-4-ylmethyl-1H-indole (600 mg, 1.68 mmol) in THF (12 mL) was cooled to −78° C. LDA (2M in THF; 1.7 mL, 3.4 mmol) was added and the mixture was stirred for 1 h. Excess solid $CO_2$ was added. After 30 min at −78° C., the reaction mixture was warmed to room temperature and 2 N HCl was added. The mixture was extracted with $CH_2Cl_2$ (3×150 mL). The organic layer was dried ($Na_2SO_4$), filtered, and evaporated to give 1-benzenesulfonyl-4-morpholin-4-ylmethyl-1H-indole-2-carboxylic acid (670 mg, 99%) as a foam which was used directly in the next step without further purification.

Step 6: 1-Benzenesulfonyl-4-morpholin-4-ylmethyl-1H-indole-2-carboxylic acid methyl ester

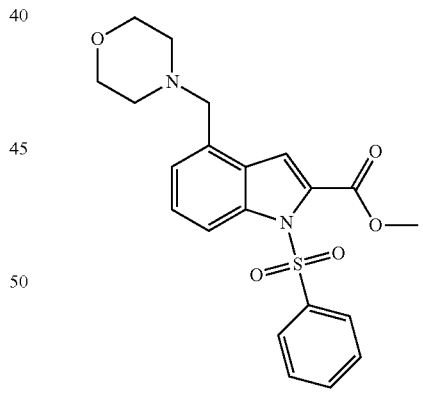

A mixture of 1-benzenesulfonyl-4-morpholin-4-ylmethyl-1H-indole-2-carboxylic acid (670 mg, 1.67 mmol) and $SOCl_2$ (10 mL, 137 mmol) was heated at reflux for 1 h. The solvent was evaporated under reduced pressure and the residue was dried under vacuum for 1 h. THF (20 mL) was added, followed by MeOH (1.5 mL) and the reaction mixture was stirred at room temperature for 1 h. The solved was evaporated under reduced pressure. The residue was purified by chromatography (silica gel, 60% EtOAc/hexanes) to give 1-benzenesulfonyl-4-morpholin-4-ylmethyl-1H-indole-2-carboxylic acid methyl ester (486 mg, 70%) as an oil.

Step 7: 3-(1-Benzenesulfonyl-4-morpholin-4-ylm-ethyl-1H-indol-2-yl)-3-oxo-propionitrile

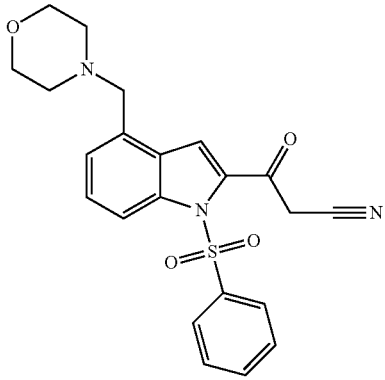 [SMILES: N#CCC(=O)c1cc2c(CN3CCOCC3)cccc2n1S(=O)(=O)c1ccccc1]

A mixture of 1-benzenesulfonyl-4-morpholin-4-ylmethyl-1H-indole-2-carboxylic acid methyl ester (486 mg, 1.17 mmol), CH$_3$CN (0.37 mL, 7.0 mmol) and THF (10 mL) was cooled to −78° C. LDA (2M in THF; 1.2 mL, 2.4 mmol) was added and the mixture was stirred at −78° C. for 30 min. Saturated aqueous NH$_4$Cl solution (10 mL) and then water (50 mL) were added. The mixture was extracted with EtOAc (350 mL). The organic layer was washed with brine, dried (Na$_2$SO$_4$), filtered, and evaporated to give 3-(1-benzenesulfonyl-4-morpholin-4-ylmethyl-1H-indol-2-yl)-3-oxo-propionitrile (506 mg, 93%) as an oil which was used directly in the next step without further purification.

Step 8: (E)-2-(1-Benzenesulfonyl-4-morpholin-4-ylmethyl-1H-indole-2-carbonyl)-3-dimethylamino-acrylonitrile

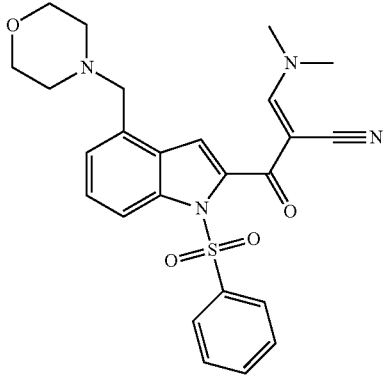 [SMILES: CN(C)/C=C(\C#N)C(=O)c1cc2c(CN3CCOCC3)cccc2n1S(=O)(=O)c1ccccc1]

A mixture of 3-(1-benzenesulfonyl-4-morpholin-4-ylmethyl-1H-indol-2-yl)-3-oxo-propionitrile (506 mg, 1.17 mmol), N,N-dimethylformamide dimethyl acetal (0.21 mL, 1.55 mmol), and toluene (10 mL) was stirred at room temperature overnight. The solvent was evaporated. The residue was purified by chromatography (silica gel, 100% EtOAc) to give (E)-2-(1-benzenesulfonyl-4-morpholin-4-ylmethyl-1H-indole-2-carbonyl)-3-dimethylamino-acrylonitrile (285 mg, 50%) as a yellow foam.

Step 9: {5-Amino-1-[4-(2,3-difluoro-phenoxy)-2-methyl-phenyl]-1H-pyrazol-4-yl}-(1-benzenesulfonyl-4-morpholin-4-ylmethyl-1H-indol-2-yl)-methanone

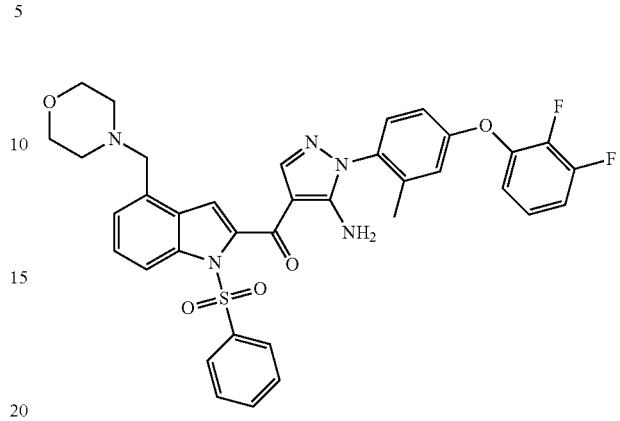

A mixture of [4-(2,3-difluoro-phenoxy)-2-methyl-phenyl]-hydrazine (which may be prepared as described for Intermediate 1; 130 mg, 0.52 mmol), (E)-2-(1-benzenesulfonyl-4-morpholin-4-ylmethyl-1H-indole-2-carbonyl)-3-dimethylamino-acrylonitrile (60 mg, 0.125 mmol), and EtOH (10 mL) was heated at reflux overnight. The solvent was removed under reduced pressure. The residue was purified by chromatography (silica gel, 50% EtOAc/hexanes) to give {5-amino-1-[4-(2,3-difluoro-phenoxy)-2-methyl-phenyl]-1H-pyrazol-4-yl}-(1-benzenesulfonyl-4-morpholin-4-ylmethyl-1H-indol-2-yl)-methanone (56 mg, 65%) as an oil.

Step 10: {5-Amino-1-[4-(2,3-difluoro-phenoxy)-2-methyl-phenyl]-1H-pyrazol-4-yl}-(4-morpholin-4-ylmethyl-1H-indol-2-yl)-methanone

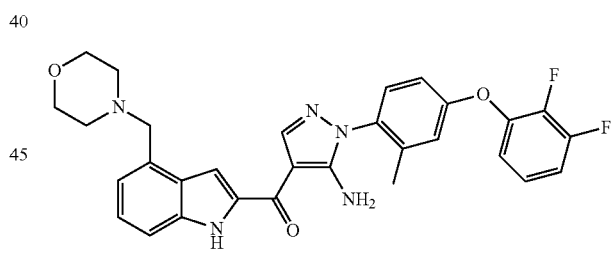

A mixture of {5-amino-1-[4-(2,3-difluoro-phenoxy)-2-methyl-phenyl]-1H-pyrazol-4-yl}-(1-benzenesulfonyl-4-morpholin-4-ylmethyl-1H-indol-2-yl)-methanone (56 mg, 0.082 mmol), Cs$_2$CO$_3$ (133 mg, 0.41 mmol), THF (4 mL) and MeOH (2 mL) was stirred at room temperature overnight. The solvent was removed under reduced pressure. The residue was purified by chromatography (silica gel, 70% EtOAc/hexanes) to give {5-amino-1-[4-(2,3-difluoro-phenoxy)-2-methyl-phenyl]-1H-pyrazol-4-yl}-(4-morpholin-4-ylmethyl-1H-indol-2-yl)-methanone (35 mg, 79%) as a light yellow oil. $^1$H NMR (400 MHz, CDCl$_3$) δ ppm 9.27 (br. s., 1 H), 8.27 (s, 1 H), 7.62 (s, 1 H), 7.39 (d, J=8.0 Hz, 1 H), 7.35 (d, J=8.5 Hz, 1 H), 7.30 (d, J=7.3 Hz, 1 H), 3.86 (br. s., 2 H), 3.75 (br. s., 4 H), 2.54 (br. s., 3 H), 2.20 (s, 3 H). MS calcd. for C$_{30}$H$_{28}$F$_2$N$_5$O$_3$ [(M+H)$^+$] 544, obsd. 544.1.

Example I-20

3-{4-[5-Amino-4-(4-cyanomethyl-1H-indole-2-carbonyl)-pyrazol-1-yl]-3-methyl-phenoxy}-benzonitrile

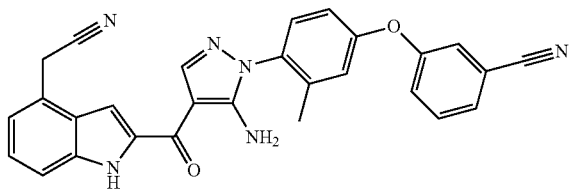 [SMILES: Cc1cc(Oc2cccc(C#N)c2)ccc1-n1ncc(C(=O)c2cc3c(CC#N)cccc3[nH]2)c1N]

Step 1: 3-{4-[5-Amino-4-(1-benzenesulfonyl-4-cyanomethyl-1H-indole-2-carbonyl)-pyrazol-1-yl]-3-methyl-phenoxy}-benzonitrile

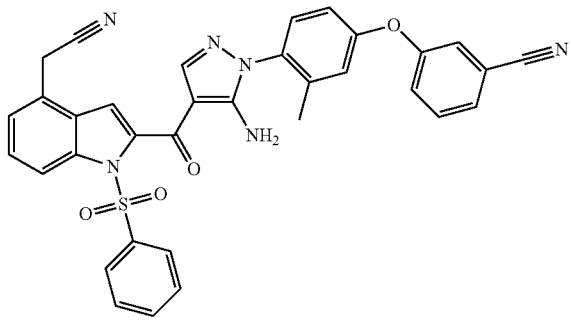 [SMILES: Cc1cc(Oc2cccc(C#N)c2)ccc1-n1ncc(C(=O)c2cc3c(CC#N)cccc3n2S(=O)(=O)c2ccccc2)c1N]

A mixture of 3-{4-[5-amino-4-(1-benzenesulfonyl-4-bromo-1H-indole-2-carbonyl)-pyrazol-1-yl]-3-methyl-phenoxy}-benzonitrile (which may be prepared as described for Example I-14 Step 1; 107 mg, 0.164 mmol), tert-butyl cyanoacetate (81 mg, 0.57 mmol), bis(tri-tert-butylphosphine)palladium(0) (Strem Chemicals; 29.5 mg, 0.058 mmol), trisodium phosphate (121 mg, 0.74 mmol) and toluene (2 mL) was heated in a sealed tube at 100° C. overnight. Water (2 mL) was added and the mixture was extracted with EtOAc (2×5 mL). The combined organic layers were evaporated. The residue was purified by chromatography (silica gel, 40% EtOAc/hexanes) to give 3-{4-[5-amino-4-(1-benzenesulfonyl-4-cyanomethyl-1H-indole-2-carbonyl)-pyrazol-1-yl]-3-methyl-phenoxy}-benzonitrile (34 mg, 34%) as an oil.

Step 2: 3-{4-[5-Amino-4-(4-cyanomethyl-1H-indole-2-carbonyl)-pyrazol-1-yl]-3-methyl-phenoxy}-benzonitrile

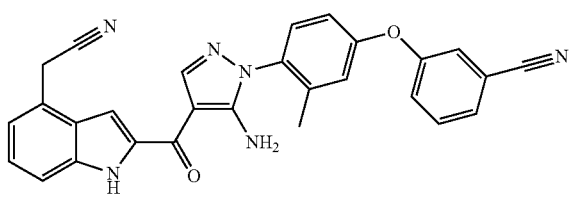 [SMILES: Cc1cc(Oc2cccc(C#N)c2)ccc1-n1ncc(C(=O)c2cc3c(CC#N)cccc3[nH]2)c1N]

A mixture of 3-{4-[5-amino-4-(1-benzenesulfonyl-4-cyanomethyl-1H-indole-2-carbonyl)-pyrazol-1-yl]-3-methyl-phenoxy}-benzonitrile (34 mg, 0.056 mmol), $Cs_2CO_3$ (81.4 mg, 0.25 mmol), THF (4 mL) and MeOH (2 mL) was stirred at room temperature overnight. The solvent was removed under reduced pressure. The residue was purified by chromatography (silica gel, 40% EtOAc/hexanes) to give 3-{4-[5-amino-4-(4-cyanomethyl-1H-indole-2-carbonyl)-pyrazol-1-yl]-3-methyl-phenoxy}-benzonitrile (11 mg, 42%) as a light yellow solid. $^1H$ NMR (400 MHz, $CDCl_3$) δ ppm 9.38 (br. s., 1 H), 8.31 (s, 1 H), 7.46-7.58 (m, 4 H), 7.31-7.45 (m, 7 H), 7.22-7.26 (m, 1 H), 6.99-7.11 (m, 3 H), 4.10 (s, 2 H), 2.25 (s, 4 H). MS calcd. for $C_{28}H_{21}N_6O_2$ [(M+H)$^+$] 473, obsd. 473.

Example I-21

2-{5-Amino-1-[4-(3-cyano-phenoxy)-2-methyl-phenyl]-1H-pyrazole-4-carbonyl}-1H-indole-4-carboxylic acid methylamide trifluoroacetate salt

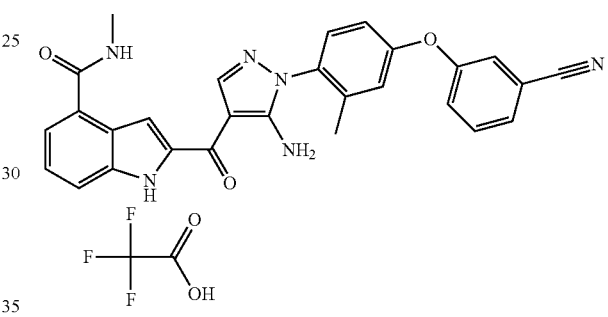

A sealed tube containing 3-{4-[5-amino-4-(4-bromo-1H-indole-2-carbonyl)-pyrazol-1-yl]-3-methyl-phenoxy}-benzonitrile (which may be prepared as described in Example I-14 Step 2; 160 mg, 0.31 mmol), $Pd(PPh_3)_4$ (108 mg, 0.094 mmol), methylamine (2 M in THF; 2 mL, 4 mmol) and THF (20 mL) was charged with 30 psi of carbon monoxide. The mixture was heated at 95° C. overnight and then the solvent was evaporated. The residue was purified by preparative HPLC to give 2-{5-amino-1-[4-(3-cyano-phenoxy)-2-methyl-phenyl]-1H-pyrazole-4-carbonyl}-1H-indole-4-carboxylic acid methylamide trifluoroacetate salt (73 mg, 48%) as an off-white lyophilized powder. $^1H$ NMR (400 MHz, $CDCl_3$) δ ppm 9.43 (s, 1 H), 8.36 (s, 1 H), 7.89 (dd, J=2.1, 0.9 Hz, 1 H), 7.60-7.64 (m, 1 H), 7.44-7.55 (m, 3 H), 7.38-7.44 (m, 2 H), 7.31-7.37 (m, 2 H), 7.07 (d, J=2.8 Hz, 1 H), 7.01 (dd, J=8.4, 2.4 Hz, 1 H), 3.15 (d, J=4.8 Hz, 3 H), 2.22 (s, 3 H). MS calcd. for $C_{28}H_{21}F_2N_6O_2$ [(M+H)$^+$] 511, obsd. 511.

Biological Examples

Bruton's Tyrosine Kinase (Btk) Inhibition Assay

The assay is a capture of radioactive $^{33}P$ phosphorylated product through filtration. The interactions of Btk, biotinylated $SH_2$ peptide substrate (Src homology), and ATP lead to phosphorylation of the peptide substrate. Biotinylated product is bound streptavidin sepharose beads. All bound, radiolabeled products are detected by scintillation counter.

Plates assayed are 96-well polypropylene (Greiner) and 96-well 1.2 μm hydrophilic PVDF filter plates (Millipore). Concentrations reported here are final assay concentrations:

10-100 µM compounds in DMSO (Burdick and Jackson), 5-10 nM Btk enzyme (His-tagged, full-length), 30 µM peptide substrate (Biotin-Aca-AAAEEIYGEI-NH$_2$), 100 µM ATP (Sigma), 8 mM imidazole (Sigma, pH 7.2), 8 mM glycerol-2-phosphate (Sigma), 200 µM EGTA (Roche Diagnostics), 1 mM MnCl$_2$ (Sigma), 20 mM MgCl$_2$ (Sigma), 0.1 mg/ml BSA (Sigma), 2 mM DTT (Sigma), 1 µCi $^{33}$P ATP (Amersham), 20% streptavidin sepharose beads (Amersham), 50 mM EDTA (Gibco), 2 M NaCl (Gibco), 2 M NaCl w/1% phosphoric acid (Gibco), microscint-20 (Perkin Elmer).

IC$_{50}$ determinations are calculated from 10 data points per compound utilizing data produced from a standard 96-well plate assay template. One control compound and seven unknown inhibitors were tested on each plate and each plate was run twice. Typically, compounds were diluted in half-log starting at 100 µM and ending at 3 nM. The control compound was staurosporine. Background was counted in the absence of peptide substrate. Total activity was determined in the presence of peptide substrate. The following protocol was used to determine Btk inhibition.

1) Sample preparation: The test compounds were diluted at half-log increments in assay buffer (imidazole, glycerol-2-phosphate, EGTA, MnCl$_2$, MgCl$_2$, BSA).
2) Bead preparation
   a.) rinse beads by centrifuging at 500 g
   b.) reconstitute the beads with PBS and EDTA to produce a 20% bead slurry
3) Pre-incubate reaction mix without substrate (assay buffer, DTT, ATP, $^{33}$P ATP) and mix with substrate (assay buffer, DTT, ATP, $^{33}$P ATP, peptide substrate) 30° C. for 15 min.
4) To start assay, pre-incubate 10 µL Btk in enzyme buffer (imidazole, glycerol-2-phosphate, BSA) and 10 µL of test compounds for 10 min at RT.
5) Add 30 µL reaction mixture without or with substrate to Btk and compounds.
6) Incubate 50 µL total assay mix for 30 min at 30° C.
7) Transfer 40 µL of assay to 150 µL bead slurry in filter plate to stop reaction.
8) Wash filter plate after 30 min, with following steps
   a. 3×250 µL NaCl
   b. 3×250 µL NaCl containing 1% phosphoric acid
   c. 1×250 µL H$_2$O
9) Dry plate for 1 h at 65° C. or overnight at RT
10) Add 50 µL microscint-20 and count $^{33}$P cpm on scintillation counter.

Calculate percent activity from raw data in cpm percent activity=(sample-$bkg$)/(total activity-$bkg$)×100

Calculate IC$_{50}$ from percent activity, using one-site dose response sigmoidal model $y=A+((B-A)/(1+((x/C)^D)))$ x=cmpd conc, y=% activity, A=min, B=max, C=IC$_{50}$, D=1 (hill slope)

Bruton's Tyrosine Kinase (BTK) Inhibition TR-FRET (Time Resolved FRET) Assay

This BTK competition assay measures compound potency (IC50) for the inactivated state of Bruton's Tyrosine Kinase using FRET (Forster/Flouresence Resonance Energy Transfer) technology. The BTK-Eu complex was incubated on ice one hour prior to use at a starting concentration of 50 nM BTK-Bioease™: 10 nM Eu-streptavidin (Perkin-Elmer Catalog# AD0062). The assay buffer consisted of 20 mM HEPES (pH 7.15), 0.1 mM DTT, 10 mM MgCl$_2$, 0.5 mg/ml BSA with 3% Kinase Stabilizer (Fremont Biosolutions, Catalog # STB-K02). After 1 h, the reaction mixture from above was diluted 10 fold in assay buffer to make 5 nM BTK: 1 nM Eu-Streptavidin complex (donor fluorophore). 18 µl of a mixture of 0.11 nM BTK-Eu and 0.11 nM Kinase Tracer 178 (Invitrogen, Catalog # PV5593,) with BTK-Eu alone as no negative control, was then dispensed into 384-well flat bottom plates (Greiner, 784076). Compounds to be tested in assay were prepared as 10× concentrations and serial dilution in half-log increments was performed in DMSO so as to generate 10 point curves. To initiate the FRET reaction, compounds prepared as 10× stock in DMSO was added to the plates and the plates were incubated 18-24 h at 14° C.

After the incubation the plates were read on a BMG Pherastar Fluorescent plate reader (or equivalent) and used to measure the emission energy from the europium donor fluorophore (620 nm emission) and the FRET (665 nm emission). The negative control well values were averaged to obtain the mean minimum. The positive "no inhibitor" control wells were averaged to obtain the mean maximum. Percent of maximal FRET was calculated using following equation:

% max FRET=100×[(FSR$_{cmpd}$-FSR$_{mean\ min}$)/(FSR$_{mean\ max}$-FSR$_{mean\ min}$)]

where FSR=FRET Signal ratio. % Max FRET curves were plotted in Activity Base (Excel) and the IC50(%), hill slope, z' and % CV were determined. The mean IC50 and standard deviation will be derived from duplicate curves (singlet inhibition curves from two independent dilutions) using Microsoft Excel.

Representative compound data for this assay are listed below in Table II.

TABLE II

| Compound | FRET IC50 (µmol) |
|---|---|
| 1 | 0.06152 |
| 2 | 0.08512 |
| 3 | 0.10574 |
| 4 | 0.0208 |
| 5 | 0.2135 |
| 6 | 0.01189 |
| 7 | 0.06531 |
| 8 | 0.00615 |
| 9 | 0.03306 |
| 10 | 0.00421 |
| 11 | 0.05911 |
| 12 | 0.20117 |
| 13 | 0.02952 |
| 14 | 0.00838 |
| 15 | 0.09358 |
| 16 | 0.03905 |
| 17 | 0.02106 |
| 18 | |
| 19 | 0.00559 |
| 20 | 0.00845 |
| 21 | 0.01302 |

Inhibition of B Cell Activation in Whole Blood Measured by CD69 Expression

A procedure to test the ability of Btk inhibitors to suppress B cell receptor-mediated activation of B cells in human blood is as follows:

Human whole blood (HWB) is obtained from healthy volunteers, with the following restrictions: 24 hr drug-free, non-smokers. Blood is collected by venipuncture into Vacutainer tubes anticoagulated with sodium heparin. Test compounds are diluted to ten times the desired starting drug concentration in PBS (20×), followed by three-fold serial dilutions in 10% DMSO in PBS to produce a nine point dose-response curve. 5.5 µl of each compound dilution is added in duplicate to a 2 ml 96-well V bottom plate (Analytical Sales and Services, #59623-23); 5.5 µl of 10% DMSO in PBS is added to control and no-stimulus wells. HWB (1000 is added to each well, and after mixing the plates are incubated at 37 C, 5% $CO_2$, 100% humidity for 30 minutes. Goat F(ab')2 anti-human IgM (Southern Biotech, #2022-14) (10 µl of a 500 µg/ml solution, 50 µg/ml final concentration) is added to each well (except the no-stimulus wells) with mixing and the plates are incubated for an additional 20 hours.

At the end of the 20 hour incubation, samples are incubated with florescent-probe-labeled anti-bodies (15 µl PE Mouse anti-Human CD20, BD Pharmingen, #555623, and/or 20 µl APC Mouse anti-Human CD69, BD Pharmingen #555533) for 30 minutes, at 37 C, 5% $CO_2$, 100% humidity. Included are induced control, unstained and single stains for compensation adjustments and initial voltage settings. Samples are then lysed with 1 ml of 1× Pharmingen Lyse Buffer (BD Pharmingen #555899), and plates are centrifuged at 1800 rpm for 5 minutes. Supernatants are removed via suction and the remaining pellets are lysed again with another 1 ml of 1× Pharmingen Lyse Buffer, and plates are spun down as before. Supernatants are aspirated and remaining pellets are washed in FACs buffer (PBS+1% FBS). After a final spin, the supernatants are removed and pellets are resuspended in 180 µl of FACs buffer. Samples are transferred to a 96 well plate suitable to be run on the HTS 96 well system on the BD LSR II flow cytometer.

Using appropriate excitation and emission wavelengths for the fluorophores used, data are acquired and percent positive cell values are obtained using Cell Quest Software. Results are initially analyzed by FACS analysis software (Flow Jo). The IC50 for test compounds is defined as the concentration which decreases by 50% the percentage of CD69-positive cells that are also CD20-positive after stimulation by anti-IgM (average of 8 control wells, after subtraction of the average of 8 wells for the no-stimulus background). The IC50 values are calculated using XLfit software version 3, equation 201.

Inhibition of B-Cell Activation—B Cell FLIPR Assay in Ramos Cells

Inhibition of B-cell activation by compounds of the present invention is demonstrated by determining the effect of the test compounds on anti-IgM stimulated B cell responses.

The B cell FLIPR assay is a cell based functional method of determining the effect of potential inhibitors of the intracellular calcium increase from stimulation by an anti-IgM antibody. Ramos cells (human Burkitt's lymphoma cell line. ATCC-No. CRL-1596) were cultivated in Growth Media (described below). One day prior to assay, Ramos cells were resuspended in fresh growth media (same as above) and set at a concentration of $0.5 \times 10^6$/mL in tissue culture flasks. On day of assay, cells are counted and set at a concentration of $1 \times 10^6$/mL1 in growth media supplemented with 1 M FLUO-3AM(TefLabs Cat-No. 0116, prepared in anhydrous DMSO and 10% Pluronic acid) in a tissue culture flask, and incubated at 37° C. (4% $CO_2$) for one h. To remove extracellular dye, cells were collected by centrifugation (5 min, 1000 rpm), resuspended in FLIPR buffer (described below) at $1 \times 10^6$ cells/mL and then dispensed into 96-well poly-D-lysine coated black/clear plates (BD Cat-No. 356692) at $1 \times 10^5$ cells per well. Test compounds were added at various concentrations ranging from 100 µM to 0.03 µM (7 concentrations, details below), and allowed to incubate with cells for 30 min at RT. Ramos cell $Ca^{2+}$ signaling was stimulated by the addition of 10 g/mL anti-IgM (Southern Biotech, Cat-No. 2020-01) and measured on a FLIPR (Molecular Devices, captures images of 96 well plates using a CCD camera with an argon laser at 480 nM excitation).

Media/Buffers:

Growth Medium: RPMI 1640 medium with L-glutamine (Invitrogen, Cat-No. 61870-010), 10% Fetal Bovine Serum (FBS, Summit Biotechnology Cat-No. FP-100-05); 1 mM Sodium Pyruvate (Invitrogen Cat. No. 11360-070).

FLIPR buffer: HBSS (Invitrogen, Cat-No. 141175-079), 2 mM $CaCl_2$ (Sigma Cat-No. C-4901), HEPES (Invitrogen, Cat-No. 15630-080), 2.5 mM Probenecid (Sigma, Cat-No. P-8761), 0.1% BSA (Sigma, Cat-No. A-7906), 11 mM Glucose (Sigma, Cat-No. G-7528)

Compound Dilution Details:

In order to achieve the highest final assay concentration of 100 µM, 24 µL of 10 mM compound stock solution (made in DMSO) is added directly to 576 µL of FLIPR buffer. The test compounds are diluted in FLIPR Buffer (using Biomek 2000 robotic pipettor) resulting in the following dilution scheme: vehicle, $1.00 \times 10^{-4}$ M, $1.00 \times 10^{-5}$, $3.16 \times 10^{-6}$, $1.00 \times 10^{-6}$, $3.16 \times 10^{-7}$, $1.00 \times 10^{-7}$, $3.16 \times 10^{-8}$.

Assay and Analysis:

Intracellular increases in calcium were reported using a max-min statistic (subtracting the resting baseline from the peak caused by addition of the stimulatory antibody using a Molecular Devices FLIPR control and statistic exporting software. The $IC_{50}$ was determined using a non-linear curve fit (GraphPad Prism software).

Mouse Collagen-Induced Arthritis (mCIA)

On day 0 mice are injected at the base of the tail or several spots on the back with an emulsion of Type II Collagen (i.d.) in Complete Freund's adjuvant (CFA). Following collagen immunization, animals will develop arthritis at around 21 to 35 days. The onset of arthritis is synchronized (boosted) by systemic administration of collagen in Incomplete Freund's adjuvant (IFA; i.d.) at day 21. Animals are examined daily after day 20 for any onset of mild arthritis (score of 1 or 2; see score description below) which is the signal to boost. Following boost, mice are scored and dosed with candidate therapeutic agents for the prescribed time (typically 2-3 weeks) and dosing frequency, daily (QD) or twice-daily (BID).

Rat Collagen-Induced Arthritis (rCIA)

On day 0, rats are injected with an emulsion of Bovine Type II Collagen in Incomplete Freund's adjuvant (IFA) is injected intradermally (i.d.) on several locations on the back. A booster injection of collagen emulsion is given around day 7, (i.d.) at the base of the tail or alternative sites on the back. Arthritis is generally observed 12-14 days after the initial collagen injection. Animals may be evaluated for the development of arthritis as described below (Evaluation of arthritis) from day 14 onwards. Animals are dosed with candidate therapeutic agents in a preventive fashion starting at the time of secondary challenge and for the prescribed time (typically 2-3 weeks) and dosing frequency, daily (QD) or twice-daily (BID).

Evaluation of Arthritis:

In both models, developing inflammation of the paws and limb joints is quantified using a scoring system that involves the assessment of the 4 paws following the criteria described below:

Scoring:

1=swelling and/or redness of paw or one digit.
2=swelling in two or more joints.

3=gross swelling of the paw with more than two joints involved.

4=severe arthritis of the entire paw and digits.

Evaluations are made on day 0 for baseline measurement and starting again at the first signs or swelling for up to three times per week until the end of the experiment. The arthritic index for each mouse is obtained by adding the four scores of the individual paws, giving a maximum score of 16 per animal.

Rat In Vivo Asthma Model

Male Brown-Norway rats are sensitized i.p. with 100 μg of OA (ovalbumin) in 0.2 ml alum once every week for three weeks (day 0, 7, and 14). On day 21 (one week following last sensitization), the rats are dosed q.d. with either vehicle or compound formulation subcutaneously 0.5 hour before OA aerosol challenge (1% OA for 45 minutes) and terminated 4 or 24 hours after challenge. At time of sacrifice, serum and plasma are collected from all animals for serology and PK, respectively. A tracheal cannula is inserted and the lungs are lavaged 3× with PBS. The BAL fluid is analyzed for total leukocyte number and differential leukocyte counts. Total leukocyte number in an aliquot of the cells (20-100 μl) is determined by Coulter Counter. For differential leukocyte counts, 50-200 μl of the sample is centrifuged in a Cytospin and the slide stained with Diff-Quik. The proportions of monocytes, eosinophils, neutrophils and lymphocytes are counted under light microscopy using standard morphological criteria and expressed as a percentage. Representative inhibitors of Btk show decreased total leucocyte count in the BAL of OA sensitized and challenged rats as compared to control levels.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

The invention claimed is:

1. A compound of Formula I,

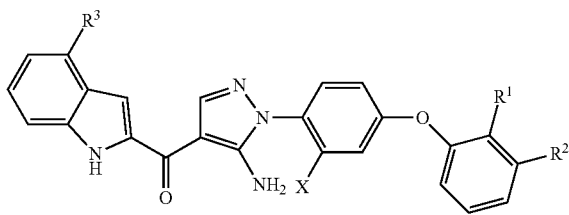

I wherein:
$R^1$ is H or halo;
$R^2$ is H, halo, or cyano;
$R^3$ is $R^4$ or $R^5$;
$R^4$ is halo or cyano;
$R^5$ is phenyl, heteroaryl, —C(=O)$R^{5'}$, lower alkyl, or benzyl, optionally substituted with one or more $R^{5'}$;
$R^{5'}$ is lower alkyl, cyano, hydroxyl, heterocycloalkyl, phenyl, amino, alkyl amino, dialkyl amino, or lower alkoxy; and
X is lower alkyl or halo;
or a pharmaceutically acceptable salt thereof.

2. The compound of claim 1, wherein X is methyl and $R^5$ is heteroaryl, optionally substituted with one or more $R^{5'}$.

3. The compound of claim 1, wherein $R^5$ is thiophenyl, optionally substituted with one or more $R^{5'}$.

4. The compound of claim 1, wherein $R^5$ is pyridyl, optionally substituted with one or more $R^{5'}$.

5. The compound of claim 1, wherein $R^1$ is F and $R^2$ is F.

6. The compound of claim 1, wherein $R^1$ is H and $R^2$ is cyano.

7. The compound of claim 1, wherein $R^5$ is —C(=O)$R^{5'}$.

8. The compound of claim 7, wherein $R^{5'}$ is morpholinyl, piperidinyl, loweralkyl-piperidinyl, or lower alkoxy.

9. The compound of claim 8, wherein $R^1$ is F and $R^2$ is F.

10. The compound of claim 8, wherein $R^1$ is H and $R^2$ is cyano.

11. The compound of claim 1, wherein $R^5$ is phenyl or benzyl, optionally substituted with one or more $R^{5'}$.

12. The compound of claim 1, wherein $R^5$ is lower alkyl, optionally substituted with one or more $R^{5'}$.

13. The compound of claim 11, wherein $R^1$ is F and $R^2$ is F.

14. The compound of claim 11, wherein $R^1$ is H and $R^2$ is cyano.

15. The compound of claim 12, wherein $R^1$ is F and $R^2$ is F.

16. The compound of claim 12, wherein $R^1$ is H and $R^2$ is cyano.

17. The compound of claim 1, selected from the group consisting of:
{5-Amino-1-[4-(2,3-difluoro-phenoxy)-2-methyl-phenyl]-1H-pyrazol-4-yl}-(4-bromo-1H-indol-2-yl)-methanone;
{5-Amino-1-[4-(2,3-difluoro-phenoxy)-2-methyl-phenyl]-1H-pyrazol-4-yl}-(4-phenyl-1H-indol-2-yl)-methanone;
{5-Amino-1-[4-(2,3-difluoro-phenoxy)-2-methyl-phenyl]-1H-pyrazol-4-yl}-(4-thiophen-3-yl-1H-indol-2-yl)-methanone;
{5-Amino-1-[4-(2,3-difluoro-phenoxy)-2-methyl-phenyl]-1H-pyrazol-4-yl}-(4-pyrazol-1-yl-1H-indol-2-yl)-methanone;
{5-Amino-1-[4-(2,3-difluoro-phenoxy)-2-methyl-phenyl]-1H-pyrazol-4-yl}-(4-thiophen-2-yl-1H-indol-2-yl)-methanone;
{5-Amino-1-[4-(2,3-difluoro-phenoxy)-2-methyl-phenyl]-1H-pyrazol-4-yl}-[4-(morpholine-4-carbonyl)-1H-indol-2-yl]-methanone;
{5-Amino-1-[4-(2,3-difluoro-phenoxy)-2-methyl-phenyl]-1H-pyrazol-4-yl}-[4-(1-methyl-1H-pyrazol-4-yl)-1H-indol-2-yl]-methanone;
{5-Amino-1-[4-(2,3-difluoro-phenoxy)-2-methyl-phenyl]-1H-pyrazol-4-yl}-(4-pyridin-2-yl-1H-indol-2-yl)-methanone;

{5-Amino-1-[4-(2,3-difluoro-phenoxy)-2-methyl-phenyl]-1H-pyrazol-4-yl}-(4-benzyl-1H-indol-2-yl)-methanone;

{5-Amino-1-[4-(2,3-difluoro-phenoxy)-2-methyl-phenyl]-1H-pyrazol-4-yl}-[4-(1H-pyrazol-4-yl)-1H-indol-2-yl]-methanone;

3-(2-{5-Amino-1-[4-(2,3-difluoro-phenoxy)-2-methyl-phenyl]-1H-pyrazole-4-carbonyl}-1H-indol-4-yl)-benzonitrile;

{5-Amino-1-[4-(2,3-difluoro-phenoxy)-2-methyl-phenyl]-1H-pyrazol-4-yl}-[4-(3-chloro-phenyl)-1H-indol-2-yl]-methanone;

3-(2-{5-Amino-1-[4-(2,3-difluoro-phenoxy)-2-methyl-phenyl]-1H-pyrazole-4-carbonyl}-1H-indol-4-ylmethyl)-benzonitrile;

3-(4-{5-Amino-4-[4-(1H-pyrazol-4-yl)-1H-indole-2-carbonyl]-pyrazol-1-yl}-3-methyl-phenoxy)-benzonitrile;

3-(4-{5-Amino-4-[4-(morpholine-4-carbonyl)-1H-indole-2-carbonyl]-pyrazol-1-yl}-3-methyl-phenoxy)-benzonitrile;

3-(4-{5-Amino-4-[4-(4-methyl-piperazine-1-carbonyl)-1H-indole-2-carbonyl]-pyrazol-1-yl}-3-methyl-phenoxy)-benzonitrile;

3-(4-{5-Amino-4-[4-(3-methoxy-benzyl)-1H-indole-2-carbonyl]-pyrazol-1-yl}-3-methyl-phenoxy)-benzonitrile;

2-{5-Amino-1-[4-(2,3-difluoro-phenoxy)-2-methyl-phenyl]-1H-pyrazole-4-carbonyl}-1H-indole-4-carboxylic acid methyl ester;

{5-Amino-1-[4-(2,3-difluoro-phenoxy)-2-methyl-phenyl]-1H-pyrazol-4-yl}-(4-morpholin-4-ylmethyl-1H-indol-2-yl)-methanone;

3-{4-[5-Amino-4-(4-cyanomethyl-1H-indole-2-carbonyl)-pyrazol-1-yl]-3-methyl-phenoxy}-benzonitrile; and 2-{5-Amino-1-[4-(3-cyano-phenoxy)-2-methyl-phenyl]-1H-pyrazole-4-carbonyl}-1H-indole-4-carboxylic acid methylamide.

18. A pharmaceutical composition, comprising the compound of claim 1, admixed with at least one pharmaceutically acceptable carrier, excipient or diluent.

19. A method for treating an inflammatory and/or autoimmune condition, mediated by Bruton's Tyrosine Kinase, comprising the step of administering to a patient in need thereof a therapeutically effective amount of the compound of claim 1.

20. A method for treating an inflammatory condition mediated by Bruton's Tyrosine Kinase, comprising the step of administering to a patient in need thereof a therapeutically effective amount of the compound of claim 1.

21. A method for treating rheumatoid arthritis, comprising the step of administering to a patient in need thereof a therapeutically effective amount of the compound of claim 1.

22. A method for treating asthma, comprising the step of administering to a patient in need thereof a therapeutically effective amount of the compound of claim 1.

* * * * *